(12) United States Patent
Evans et al.

(10) Patent No.: US 11,957,393 B2
(45) Date of Patent: Apr. 16, 2024

(54) LOCKING VARIABLE LENGTH COMPRESSION SCREW

(71) Applicant: GLOBUS MEDICAL, INC., Audubon, PA (US)

(72) Inventors: Peter Evans, Lafayette Hill, PA (US); Jonan Philip, Phoenixville, PA (US); Barclay Davis, Glenmoore, PA (US); David Laird, Sr., Honey Brook, PA (US); Thomas Zamorski, Conshohocken, PA (US)

(73) Assignee: Globus Medical, Inc., Audubon, PA (US)

( * ) Notice: Subject to any disclaimer, the term of this patent is extended or adjusted under 35 U.S.C. 154(b) by 245 days.

(21) Appl. No.: 17/314,172

(22) Filed: May 7, 2021

(65) Prior Publication Data
US 2021/0353343 A1   Nov. 18, 2021

Related U.S. Application Data

(60) Provisional application No. 63/023,291, filed on May 12, 2020.

(51) Int. Cl.
*A61B 17/86* (2006.01)
*A61B 17/04* (2006.01)
*A61B 17/68* (2006.01)

(52) U.S. Cl.
CPC ...... *A61B 17/8645* (2013.01); *A61B 17/8635* (2013.01); *A61B 2017/044* (2013.01); *A61B 2017/681* (2013.01)

(58) Field of Classification Search
CPC ............ A61B 17/8645; A61B 17/8685; A61B 17/8883
See application file for complete search history.

(56) References Cited

U.S. PATENT DOCUMENTS

| | | | |
|---|---|---|---|
| 1,210,669 | A | 1/1917 | Mike et al. |
| 2,411,761 | A | 11/1946 | Stolberg |
| 4,175,555 | A | 11/1979 | Herbert |
| 4,432,358 | A | 2/1984 | Fixel |
| 4,456,005 | A | 6/1984 | Lichty |

(Continued)

FOREIGN PATENT DOCUMENTS

| | | |
|---|---|---|
| CN | 103054642 A | 4/2013 |
| JP | S57146936 A | 9/1982 |

(Continued)

*Primary Examiner* — Olivia C Chang

(57) ABSTRACT

A variable length headless compression screw insertion system includes a compression screw and a driver assembly for driving the compression screw into a bone. The compression screw has a bone screw and a compression sleeve coupled to the bone screw. The bone screw includes a proximal end having an external threading threadably received in the compression sleeve, and the compression sleeve includes a proximal end having a predefined drive feature and an external threading. The driver assembly includes a sleeve coupler adapted to threadably receive the external threading of the compression sleeve. A ram driver is coupled to the sleeve coupler and has a predetermined length such that its distal end is shaped to contact the proximal end of the bone screw to prevent translation of the bone screw relative to the compression sleeve.

8 Claims, 18 Drawing Sheets

(56) References Cited

U.S. PATENT DOCUMENTS

| | | |
|---|---|---|
| 4,640,271 A | 2/1987 | Lower |
| 4,858,601 A | 8/1989 | Glisson |
| 4,940,467 A | 7/1990 | Tronzo |
| 5,197,841 A | 3/1993 | Tanaka |
| 5,217,462 A | 6/1993 | Asnis et al. |
| 5,234,300 A | 8/1993 | Fluckiger |
| 5,411,523 A | 5/1995 | Goble |
| 5,498,265 A | 3/1996 | Asnis et al. |
| 5,527,312 A | 6/1996 | Ray |
| 5,573,548 A | 11/1996 | Nazre et al. |
| 5,697,929 A | 12/1997 | Mellinger |
| 5,743,912 A | 4/1998 | Lahille et al. |
| 5,871,486 A | 2/1999 | Huebner et al. |
| 5,904,704 A | 5/1999 | Goble et al. |
| 6,030,162 A | 2/2000 | Huebner |
| 6,059,786 A | 5/2000 | Jackson |
| 6,074,391 A | 6/2000 | Metz-Stavenhagen et al. |
| 6,319,254 B1 | 11/2001 | Giet et al. |
| 6,319,269 B1 | 11/2001 | Li |
| 6,368,319 B1 | 4/2002 | Schaefer |
| 6,485,518 B1 | 11/2002 | Cornwall et al. |
| 6,540,747 B1 | 4/2003 | Marino |
| 6,547,795 B2 | 4/2003 | Schneiderman |
| 6,648,893 B2 | 11/2003 | Dudasik |
| 6,669,698 B1 | 12/2003 | Tromanhauser et al. |
| 6,730,089 B2 | 5/2004 | Jackson |
| 6,730,093 B2 | 5/2004 | Saint Martin |
| 6,808,526 B1 | 10/2004 | Mageri et al. |
| 6,887,243 B2 | 5/2005 | Culbert |
| 6,951,561 B2 | 10/2005 | Warren et al. |
| 6,964,664 B2 | 11/2005 | Freid et al. |
| 7,044,483 B2 | 5/2006 | Capanni |
| 7,044,953 B2 | 5/2006 | Capanni |
| 7,371,238 B2 | 5/2008 | Soboleski et al. |
| 7,582,107 B2 | 9/2009 | Trail et al. |
| 7,794,483 B2 | 9/2010 | Capanni |
| D625,183 S | 10/2010 | Bartsch et al. |
| D639,653 S | 6/2011 | Kanda et al. |
| 8,099,833 B2 | 1/2012 | Duan et al. |
| 8,956,356 B2 | 2/2015 | Zurschmiede |
| 9,247,963 B2 | 2/2016 | Kollmer |
| D797,937 S | 9/2017 | Dacosta et al. |
| 9,795,412 B2 | 10/2017 | Sinha |
| 9,820,788 B2 | 11/2017 | Vrionis et al. |
| 9,907,576 B2 | 3/2018 | Mahajan et al. |
| 9,980,762 B2 | 5/2018 | Anapliotis |
| 10,456,182 B2 | 10/2019 | Dacosta et al. |
| 10,478,238 B2 | 11/2019 | Palmer et al. |
| 2003/0045881 A1 | 3/2003 | Barouk et al. |
| 2004/0068261 A1 | 4/2004 | Fourcault et al. |
| 2004/0260298 A1 | 12/2004 | Kaiser et al. |
| 2005/0143735 A1 | 6/2005 | Kyle |
| 2005/0149030 A1 | 7/2005 | Serhan et al. |
| 2005/0203522 A1 | 9/2005 | Vaughan |
| 2006/0085068 A1 | 4/2006 | Barry |
| 2006/0200137 A1 | 9/2006 | Soboleski et al. |
| 2006/0276790 A1 | 12/2006 | Dawson et al. |
| 2007/0112428 A1 | 5/2007 | Lancial |
| 2007/0118132 A1 | 5/2007 | Culbert et al. |
| 2009/0192551 A1 | 7/2009 | Cianfrani et al. |
| 2013/0041414 A1 | 2/2013 | Epperly et al. |
| 2013/0338722 A1 | 12/2013 | Yalizis |
| 2015/0150615 A1 | 6/2015 | Anapliotis |
| 2015/0250515 A1 | 9/2015 | Terrill et al. |
| 2015/0327902 A1* | 11/2015 | Eekhoff ............ A61B 17/8891 606/310 |
| 2016/0287301 A1 | 10/2016 | Mehl et al. |
| 2018/0008317 A1 | 1/2018 | Sinha |
| 2018/0071000 A1 | 3/2018 | Pham et al. |
| 2018/0185019 A1 | 7/2018 | Lunn et al. |
| 2019/0008570 A1 | 1/2019 | Rowe et al. |

FOREIGN PATENT DOCUMENTS

| | | |
|---|---|---|
| JP | H08206128 A | 8/1996 |
| JP | H10509333 A | 9/1998 |
| JP | 200433767 A | 2/2004 |
| JP | 2005065760 A | 3/2005 |
| JP | 2006504505 A | 2/2006 |
| JP | 2006187633 A | 7/2006 |
| JP | 2012024177 A | 2/2012 |
| JP | 2015533583 A | 11/2015 |
| JP | 2017084209 A | 5/2017 |
| JP | 2018011936 A | 1/2018 |
| JP | 2019517851 A | 6/2019 |
| WO | 2004008949 A2 | 1/2004 |
| WO | 2004069031 A2 | 8/2004 |
| WO | 2004098453 A2 | 11/2004 |

* cited by examiner

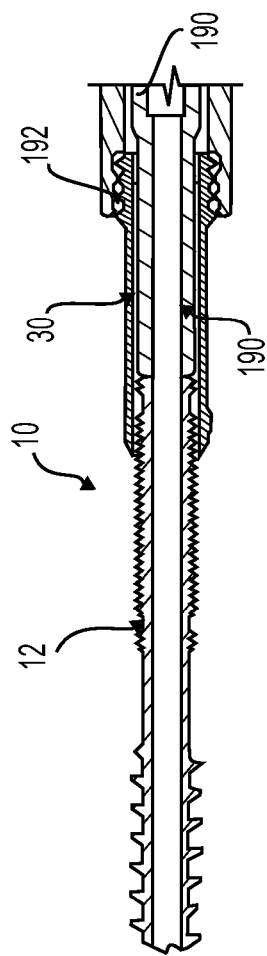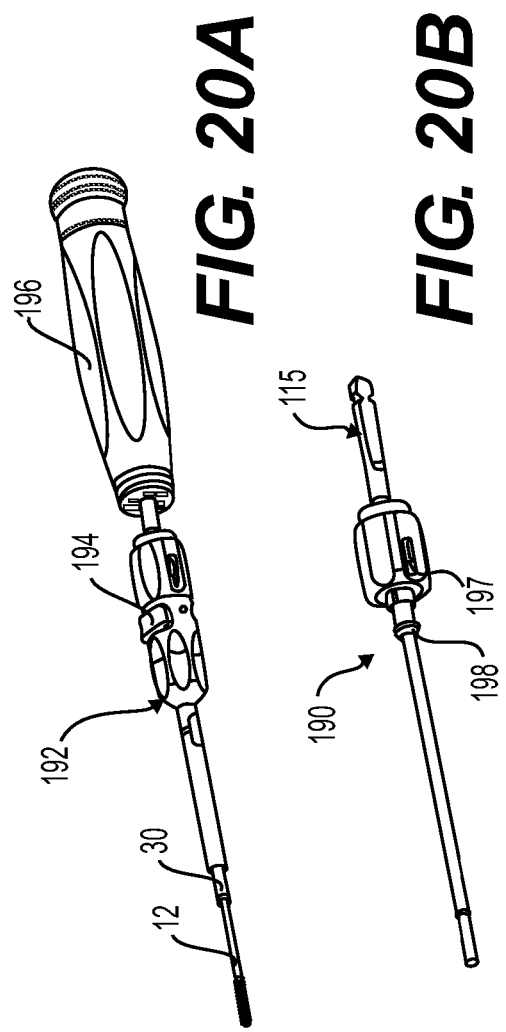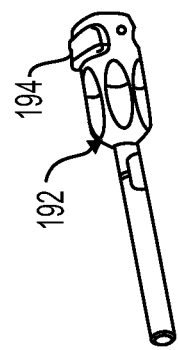
FIG. 19
FIG. 20A
FIG. 20B
FIG. 20C

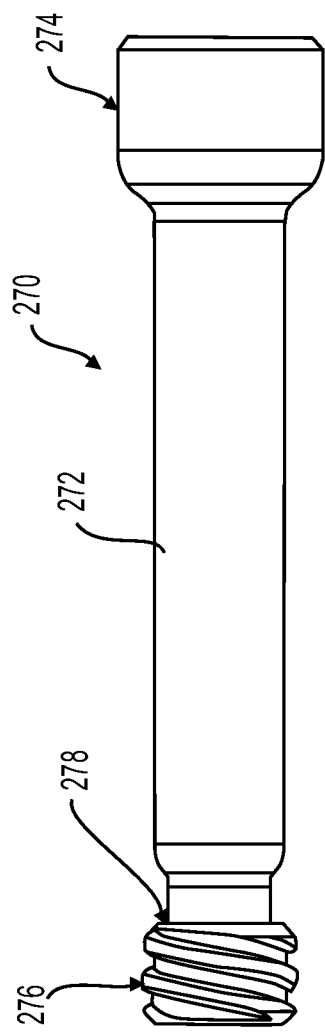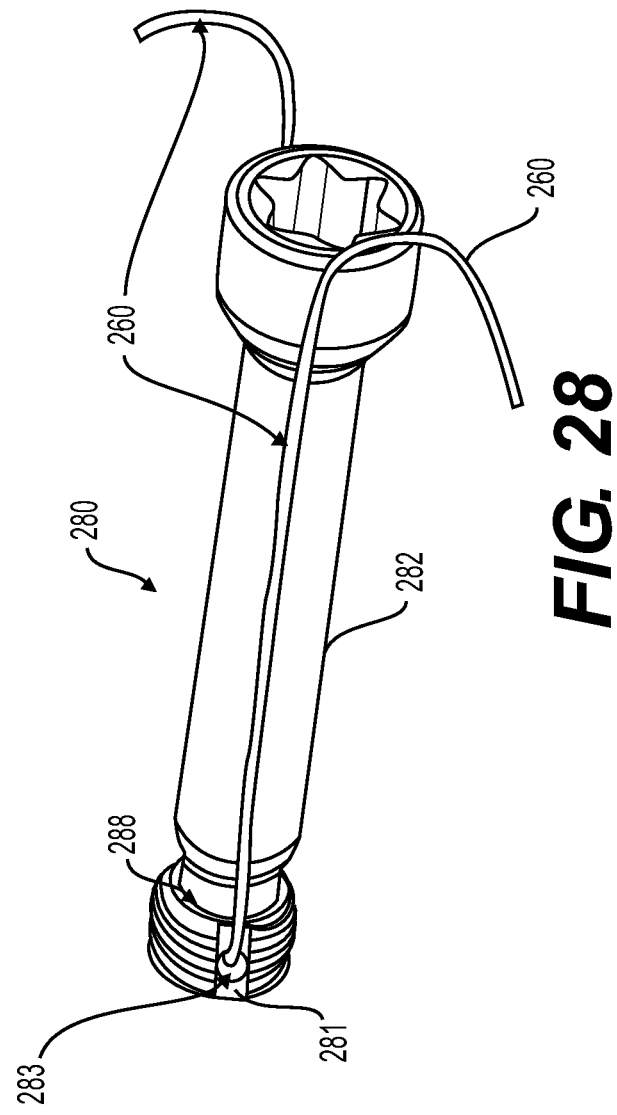

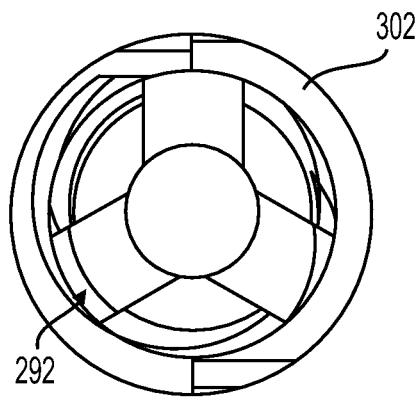
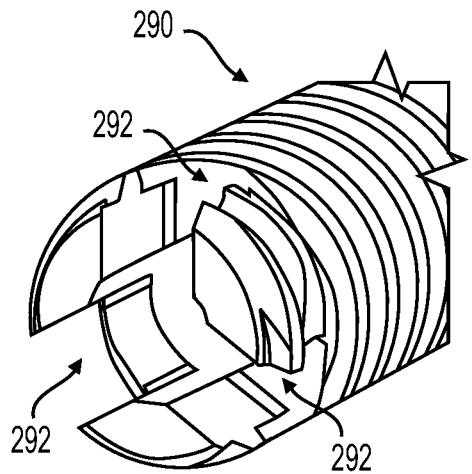
FIG. 29A  FIG. 29B
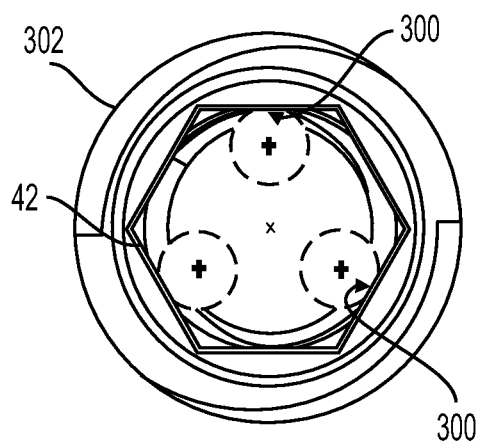
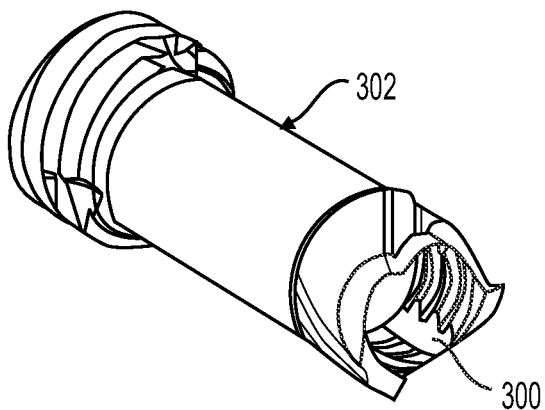
FIG. 30A  FIG. 30B

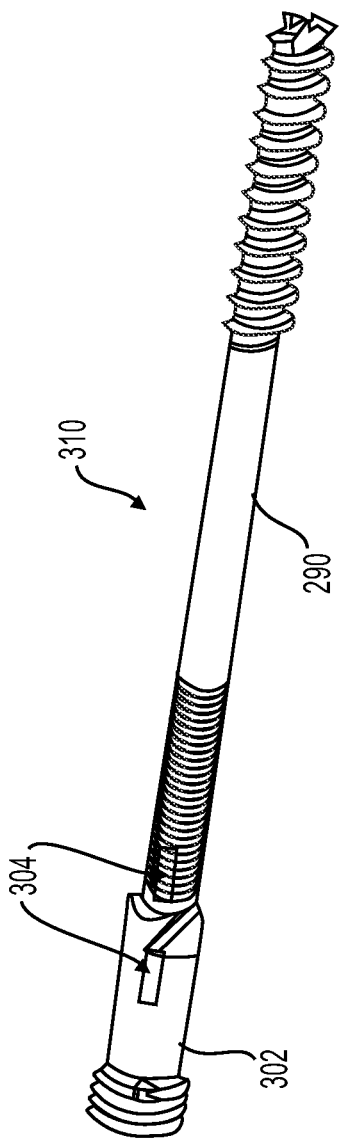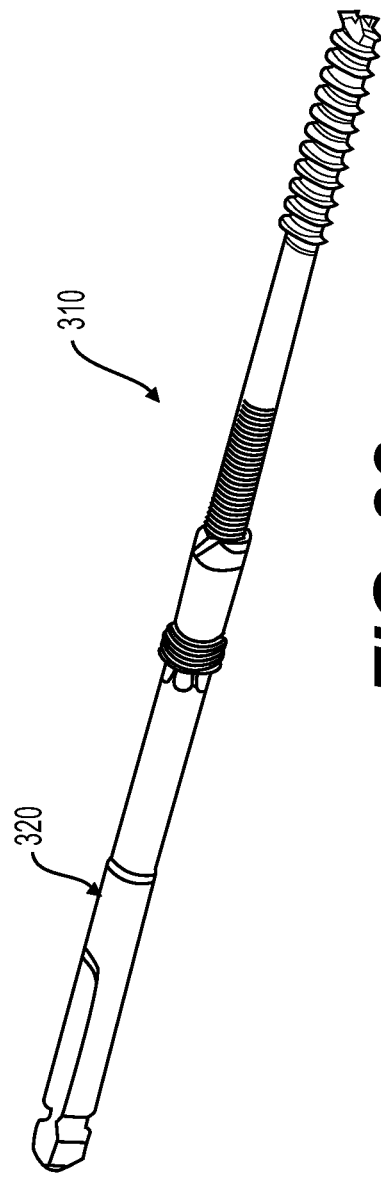

LOCKING VARIABLE LENGTH COMPRESSION SCREW

CROSS REFERENCE TO RELATED APPLICATIONS

The present invention claims priority to U.S. Provisional Patent Application No. 63/023,291, filed May 12, 2020, which is incorporated herein by reference in its entirety.

FIELD OF THE INVENTION

The present disclosure relates to implantable screws. More particularly, the disclosure relates to implantable screws configured to provide compression upon a bone into which the screw is implanted.

BACKGROUND OF THE INVENTION

A broken bone must be carefully stabilized and supported until it is strong enough to handle the body's weight and movement. Until the last century, physicians relied on casts and splints to support and stabilize the bone from outside the body. The advent of sterile surgical procedures reduced the risk of infection, allowing doctors to internally set and stabilize fractured bones. During a surgical procedure to set a fracture, the bone fragments are first repositioned (reduced) into their normal alignment. They are held together with special implants, such as plates, screws, nails and wires.

Screws are used for internal fixation more often than any other type of implant. Although the screw is a simple device, there are different designs based on the type of fracture and how the screw will be used. Screws come in different sizes for use with bones of different sizes. Screws can be used alone to hold a fracture, as well as with plates, rods, or nails. After the bone heals, screws may be either left in place or removed.

In many instances, it is desired that the inserted screw provide compression at the bone joint or fracture line to reduce the incidence of nonunion (improper healing) and malunion (healing in improper position) of broken bones.

SUMMARY OF THE INVENTION

To meet this and other needs, devices, systems, and methods for fixating bone are provided. In particular, bone screws are provided that apply compression to bone fragments or bone portions (for example, fixation of fractures or fusion of joints), are self-tapping and/or self-drilling, minimize or prevent screw toggle and/or back-out, remove bone build-up (for example, from cutting flutes), and the like.

In at least one embodiment, a variable length headless compression screw insertion system includes a compression screw and a driver assembly for driving the compression screw into a bone. The compression screw has a bone screw and a compression sleeve coupled to the bone screw. The bone screw includes a proximal end having an external threading threadably received in the compression sleeve, and the compression sleeve includes a proximal end having a predefined drive feature and an external threading. The driver assembly includes a sleeve coupler adapted to threadably receive the external threading of the compression sleeve. A ram driver is coupled to the sleeve coupler and has a predetermined length such that its distal end is shaped to contact the proximal end of the bone screw to prevent translation of the bone screw relative to the compression sleeve.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 19 is a cross-sectional view of a sleeve coupler attached to a compression screw and a ram driver according to an aspect of the present invention.

FIG. 20A is a perspective view of a compression screw and a fully assembled driver assembly including a sleeve coupler and a ram driver of FIG. 20B.

FIG. 20B is a perspective view of a ram driver according to an aspect of the present invention.

FIG. 20C is a perspective view of a sleeve coupler.

FIG. 27 is a perspective view of a breakaway jam screw 270.

FIG. 28 is a perspective view of a suture breakaway jam screw 280 having a shaft 282, jamming screw 286, and breakaway region 288.

FIGS. 29A and 29B are top view and perspective view of a bone screw, respectively, according to another aspect of the present invention.

FIGS. 30A and 30B are top view and perspective view of a compression sleeve that mates with the bone screw of FIGS. 29A and 29B.

FIG. 31 is a perspective view of a compression screw having alignment marks according to another aspect of the present invention.

FIG. 32 is a perspective view of a compression screw of FIG. 31 with a driver that locks a compression sleeve and a bone screw together according to another aspect of the present invention.

DETAILED DESCRIPTION OF THE INVENTION

Figure 1:
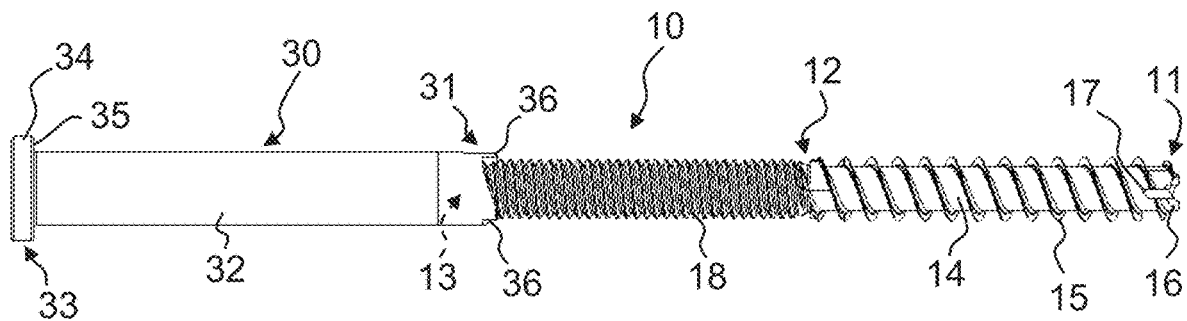
FIG. 1 is a plan view of a compression screw according to an embodiment of the invention.

In the drawings, like numerals indicate like elements throughout. Certain terminology is used herein for convenience only and is not to be taken as a limitation on the present invention. The following describes preferred embodiments of the present invention. However, it should be understood, based on this disclosure, that the invention is not limited by the preferred embodiments described herein.

Figure 2:
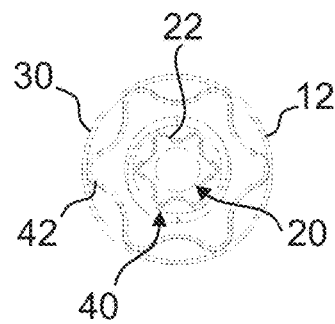
FIG. 2 is an end view of the compression screw of FIG. 1.
Figure 8:
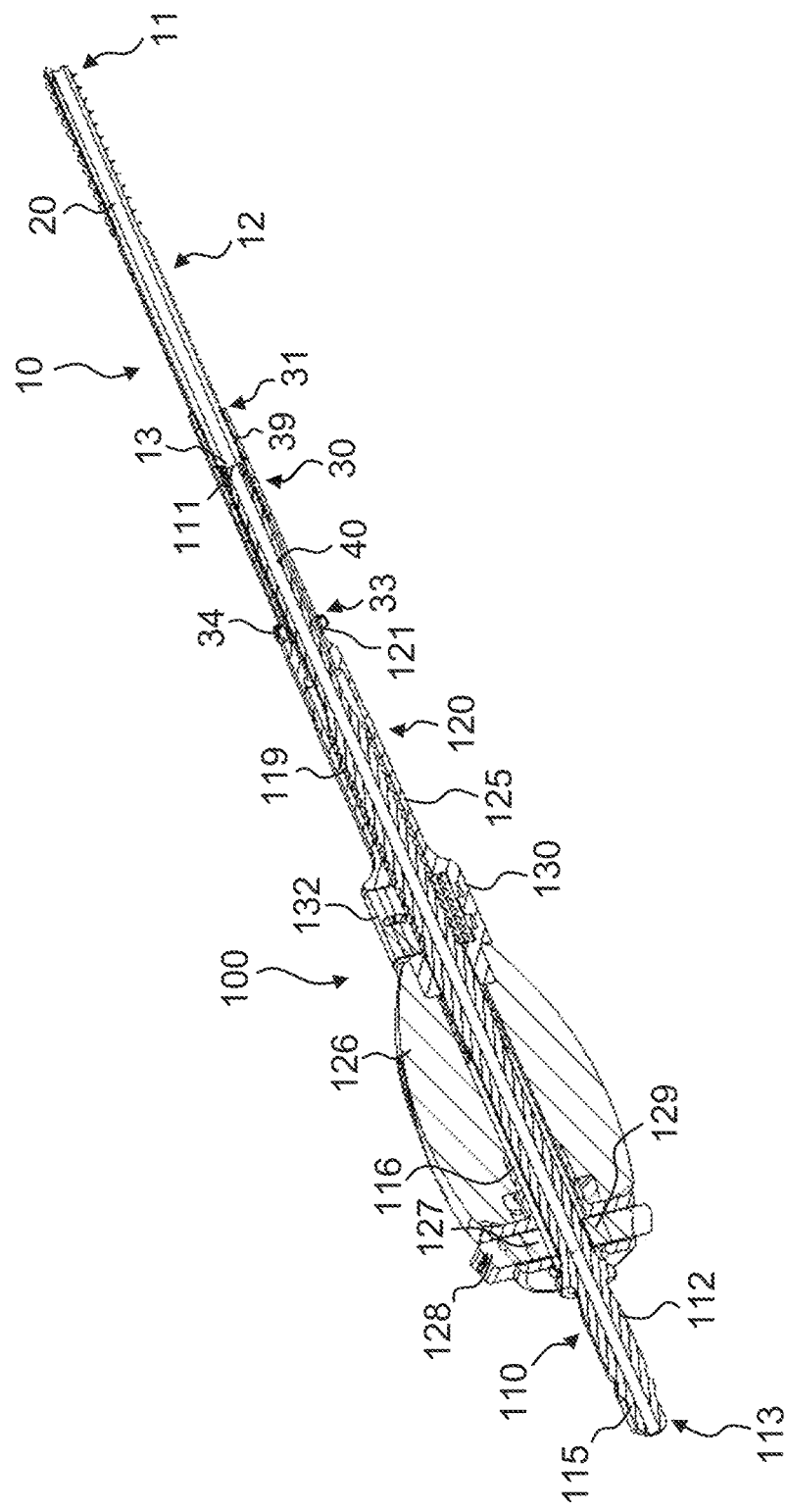
FIG. 8 is a cross-sectional view of the driver assembly of FIG. 7 engaged with the compression screw of FIG. 1.

Referring to FIGS. 1-2 and 8, a compression screw 10 in accordance with an embodiment will be described. The compression screw 10 generally comprises a bone screw 12 and a compression sleeve 30. The bone screw 12 and the compression sleeve 30 may be constructed from any biocompatible material including, but not limited to, stainless steel alloys, titanium, titanium based alloys, or polymeric materials.

The bone screw 12 includes a shaft 14 extending from a distal end 11 to a proximal end 13. Referring to FIGS. 2 and 8, in the illustrated embodiment, a cannula 20 extends from the distal end 11 to the proximal end 13 such that a guide wire may be used for positioning the compression screw 10. A drive feature 22 is defined in the proximal end 13 of the shaft 14 and is configured and dimensioned to be any shape that corresponds with the end of the driving instrument designed to engage the bone screw 12. As an example, in the illustrated embodiment, the drive feature 22 has a hexalobular configuration.

A series of bone engaging threads 15 extend radially from the shaft 14 at the distal end 11 and a series of sleeve engaging threads 18 extend radially from the shaft 14 at the proximal end 13. In the preferred embodiment, the bone engaging threads 15 are dual lead thread type and the sleeve engaging threads 18 are a standard machine thread. However, any type of thread for either thread series 15, 18 may be used to facilitate the function of the compression screw 10. The bone screw 12 preferably also includes at least one cutting flute 16 configured to cut into the bone as the bone screw 12 is rotated, defining a self-drilling and self-tapping tip. In a preferred embodiment, a slot 17 is associated with each cutting flute 16 to clear any chips, dust, or debris generated when the compression screw 10 is implanted into bone tissue.

The compression sleeve 30 includes a tubular body 32 extending from a distal end 31 to a proximal end 31 with an internal passage 40 therethrough. The compression sleeve 30 includes a series of internal threads 39 (see FIG. 8) configured to engage the sleeve engaging threads 18 of the bone screw 12 such that the bone screw 12 and the compression sleeve 30 are threadably adjustable to one another. The proximal end 33 of the compression sleeve 30 defines a radially extending head 34 which defines a shoulder 35 between the tubular body 32 and the head 34. A drive feature 42 is defined in the head 34 of the compression sleeve 30 and is configured and dimensioned to be any shape that corresponds with the end of the driving instrument designed to engage the compression sleeve 30. As an example, in the illustrated embodiment, the drive feature 42 has a hexalobular configuration.

As will be described in more detail hereinafter, during insertion of the implant, both drive features 22, 42 are engaged such that the compression screw 10 maintains its full length. After the tip of the bone screw 12 is at the desired depth, only the drive feature 42 in the compression sleeve 30 is actuated. Since the two components are connected via threads, actuation of only the compression sleeve 30 will act to move the compression sleeve 30 distally toward the tip of the bone screw 12, which shortens the length of the compression screw 10 and compresses the bone when the shoulder 35 of the compression sleeve 30 is on the near cortex.

To facilitate such shortening of the compression screw 10, the distal end 31 of the compression sleeve 30 is provided with one or more cutting flutes 36 configured to cut into the bone as the compression sleeve 30 is rotated. The cutting flutes 36 simplify the procedure by removing material without the necessity of drilling to the outer diameter of the compression sleeve tubular body 32. This also allows the compression screw 10 to be adjusted to any length without the need to predrill to a desired depth to accommodate the compression sleeve 30. In the present embodiment, the cutting flutes 36 define a proximal rotary cutting structure.

Figure 3:
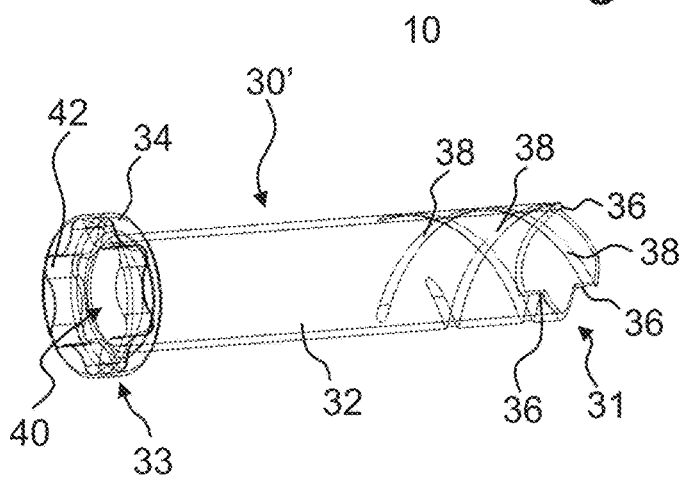
FIG. 3 is a perspective view of a compression sleeve in accordance with another exemplary embodiment.
Figure 4:
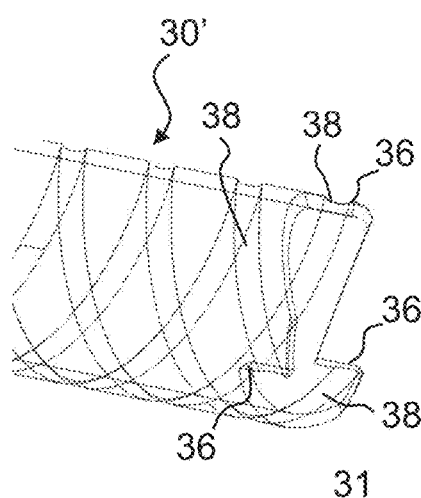
FIG. 4 is an expanded view of the cutting end of the compression sleeve of FIG. 3.

In the alternative embodiment of the compression sleeve 30' illustrated in FIGS. 3 and 4, a slot 38 is associated with each cutting flute 36, with each slot recessed into the surface of the tubular body 32 and configured to guide the aforementioned cut bone into the slots 38. The mechanism of action for this technology relies on first the cutting flutes 36 to remove material from the substrate that it is being inserted into. This material then follows through the path of the slots 38 by one of two mechanisms: (1) path of least resistance (the material has nowhere else to go) or (2) the trajectory of the slots 38 roughly follows the pitch of the cutting flutes 36 as it is advanced into the bone, and thus the cutaway material stays close to its original position as the screw advances axially via the screw's helix.

The slots 38 serve two functions: (1) the cut bone that follows the slots 38 acts to enhance the fit between the native bone and the component being inserted into the bone and (2) allows for bony ingrowth to prevent dislodging of the compression screw 10. The cutting flutes 36 act to remove bone and guide said removed bone into the slots 38. This is in effect a self-grafting feature of the compression sleeve 30 which enhances purchase. Surgeons will sometimes remove bone and pack it back into the implant to enhance purchase, however, this configuration on the compression sleeve 30 does that for them. Enhanced purchase acts to prevent screw toggle and screw axial motion. Even if the slots 38 are not filled with bone, they can act to prevent both screw toggle and screw axial motion by providing a surface to catch on the native bone. Additionally, the slots 38 provide a surface for bony ingrowth which can also prevent screw toggle and screw axial motion.

Figure 5:
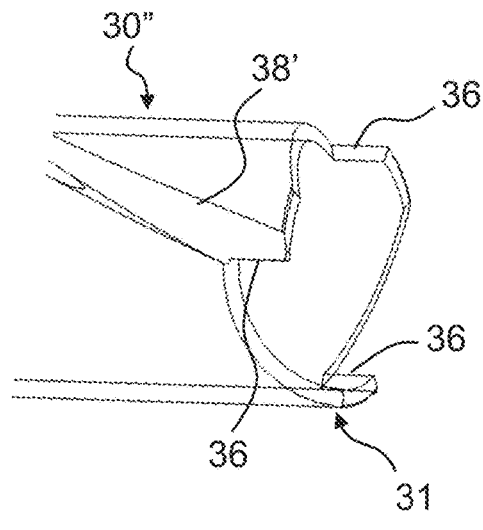
FIG. 5 is an expanded view of the cutting end of a compression sleeve in accordance with another exemplary embodiment.
Figure 6:
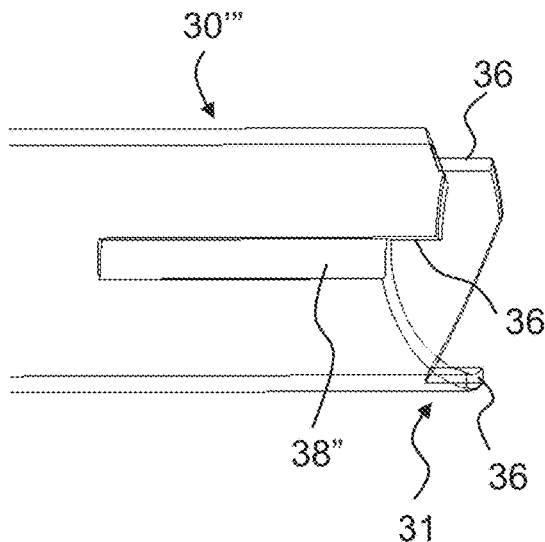
FIG. 6 is an expanded view of the cutting end of a compression sleeve in accordance with yet another exemplary embodiment.

While the trajectory of the slots 38 is shown in the embodiment of FIGS. 3 and 4 to roughly follow the pitch of the cutting flutes 36, the slots may have other configurations. For example, in the compression sleeve 30" illustrated in FIG. 5, the slot 38' has a steeper trajectory than the pitch of the cutting flutes. FIG. 6 illustrates another embodiment of the compression sleeve 30''' wherein the slot 38" has an even steeper trajectory, being substantially parallel to the axis of the compression sleeve 30'''. In addition to having different trajectories, the slots 38, 38', 38" may have different pitches resulting in the slots being spaced closer together or further apart. Additionally, the slots 38, 38', 38" may have different configurations, for example, semi-circular, semi-oval, v-shaped, square, rectangular or the like. Furthermore, while the combination of cutting flutes 36 and slots 38, 38', 38" are illustrated in conjunction with the compression sleeve 30, it is recognized that such can be applied to a surface of any type of component that is being inserted into bone.

Figure 7:
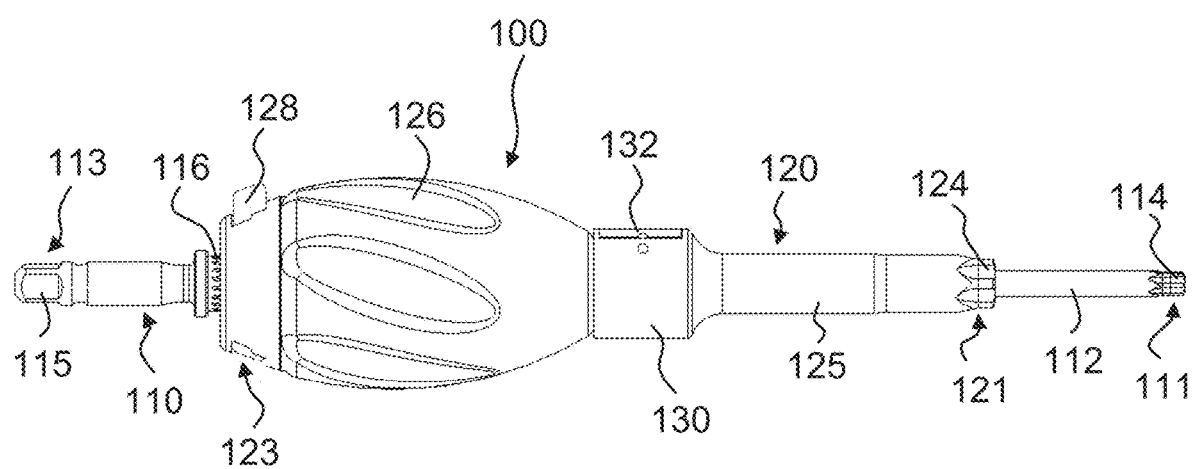
FIG. 7 is a plan view of an exemplary driver assembly configured for implantation of the compression screw of FIG. 1.

Having generally described the compression screw 10, an exemplary driver assembly 100 for inserting the compression screw 10 and an exemplary method of insertion will be described with reference to FIGS. 7 and 8.

The driver assembly 100 has a bone screw driver 110 and a compression sleeve driver 120. The bone screw driver 110 includes a driver shaft 112 extending from a distal end 111 to a proximal end 113. A driver tip 114 is defined on the distal end 111 of the driver shaft 112 and is configured to engage the driver feature 22 of the bone screw 12. A connection key 115 is defined on the proximal end 113 of the driver shaft 112 and is configured to facilitate connection of the bone screw driver 110 to a manual or powered rotation device or a locking device which prevents rotation (not shown). A series of axial splines 116 extend radially from the driver shaft 112 and are configured to be selectively engaged by a connector switch 128 of the compression sleeve driver 120, as will be described in more detail hereinafter. A series of external threads 119 extend from the driver shaft 112 distally of the splines 116. The external threads 119 are configured to be selectively engaged by a thread engagement member 132 of the compression sleeve driver 120, as will be described in more detail hereinafter.

The compression sleeve driver 120 extends from a distal end 121 to a proximal end 123. The proximal end 121 is defined by a tubular body 125 with a driver tip 124 at the distal most end and an outward housing 130 proximally therefrom. The driver tip 124 is configured to engage the driver feature 42 of the compression sleeve 30. The housing 130 defines a radial chamber in which the thread engagement member 132 is radially moveable. Upon depression of the thread engagement member 132, internal threads thereof engage the external threads 119 of the driver shaft 112 such that the driver shaft 112 is caused to move axially with the compression sleeve driver 120 when they are rotated together as will be described.

A handle member 126 extends proximally from the housing 130 to the proximal end 123. The connector switch 128 extends transversely through the handle member 126 and is moveable between a non-engaged position (see FIG. 8) and an engaged position (see FIG. 13). In the non-engaged position, an open area 129 of the connector switch 128 aligns with the splines 116 such that the switch 128 is not engaged with the splines 116 and the compression sleeve driver 120 rotates independent of the bone screw driver 110. In the engaged position, a contact portion 127 of the connector switch 128 engages the splines 116 such that rotation of the compression sleeve driver 120 causes simultaneous rotation of the bone screw driver 110.

To insert the compression screw 10, the driver assembly 100 is positioned such that the driver tip 114 of the shaft 112 engages with the drive feature 22 of the bone screw 12 and the driver tip 124 of the tubular body 125 engages with the drive feature 42 of the compression sleeve 30, as shown in FIG. 8. During initial insertion, the connector switch 128 is moved to the engaged position such that the bone screw driver 110 and the compression sleeve driver 120 rotate together. The driver assembly 100 is rotated with both drivers 110, 120 rotating and thus the compression screw 10 is advanced as a single unit until the distal end 11 of the bone screw 12 is at a desired location. The thread engagement member 132 may be depressed during such rotation to ensure that the shaft 112 advances axially during the simultaneous rotation. If the distal end 31 of the compression sleeve 30 contacts bone as the compression screw 10 is advanced, the proximal rotary cutting structure, i.e. the cutting flutes 36, cut into the bone and the compression screw 10 is free to continue to advance as a single unit.

After the distal end 11 of the bone screw 12 has landed at the desired location, compression may be achieved by advancing the compression sleeve 30 while the bone screw 12 remains stationary. The bone screw 12 remains stationary by holding the bone screw driver 110 stationary, for example, by attaching a locking device to the connection key 115, and by disengaging the connector switch 128. With the connector switch 128 moved to the disengaged position, the compression sleeve driver 120 rotates freely about the bone screw driver 110. Rotation of the compression sleeve driver 120 causes the compression sleeve 30 to advance. Since the bone screw 12 is stationary as the compression sleeve driver 120 advances the compression sleeve 30, the compression screw 10 shortens in length and the shoulder 35 thus applies compression. Again, the cutting flutes 36 on the compression sleeve distal end 31 allow the compression sleeve 30 to cut into and advance into the bone.

Figure 9:
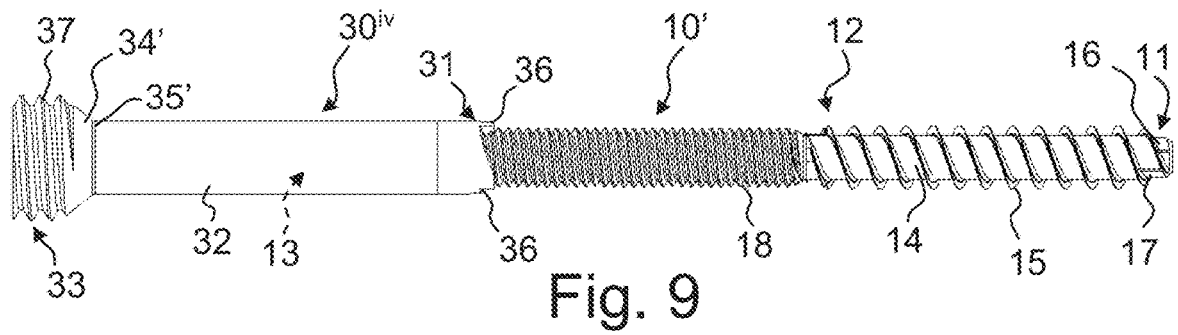
FIG. 9 is a plan view of a compression screw according to another embodiment of the invention.
Figure 10:
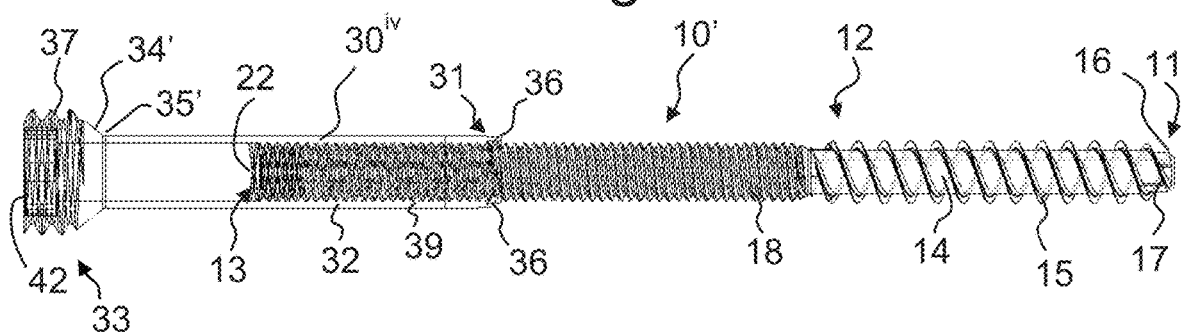
FIG. 10 is a plan view similar to FIG. 9 with the compression sleeve shown transparently.

Referring to FIGS. 9-10, a compression screw 10' in accordance with another exemplary embodiment will be described. The compression screw 10' is substantially the same as the previous embodiment except with the addition of a self-countersinking head 34' on the compression sleeve 30$^{iv}$. The self-countersinking head 34' has a tapered shoulder 35' and a series of external threads 37. The threads 37 are configured to be self-drilling and self-tapping. The self-countersinking head 34' is advantageous in that the head does not protrude from the near cortex, which minimizes soft-tissue irritation and can reduce the reoperation rate. In the present embodiment, the cutting flutes 36 and the threads 37 each define a proximal rotary cutting structure. In all other aspects, the compression screw 10' is the same as the previously described compression screw 10.

Figure 11:
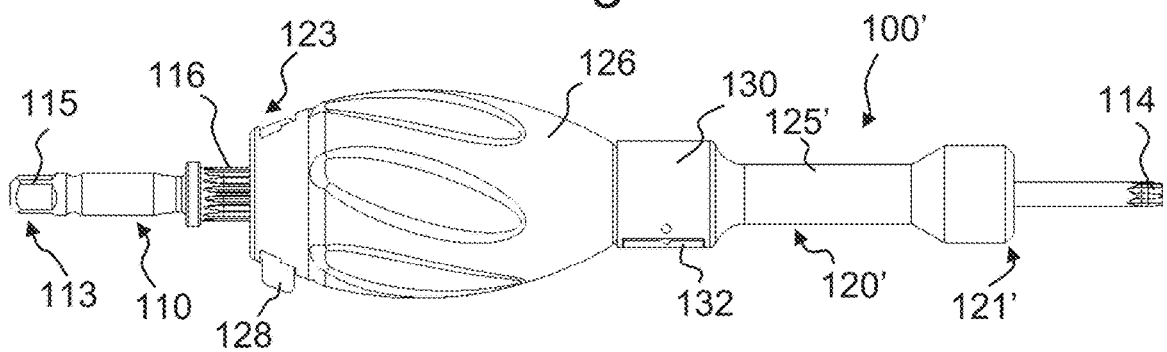
FIG. 11 is a plan view of an exemplary driver assembly configured for implantation of the compression screw of FIG. 9.
Figure 12:
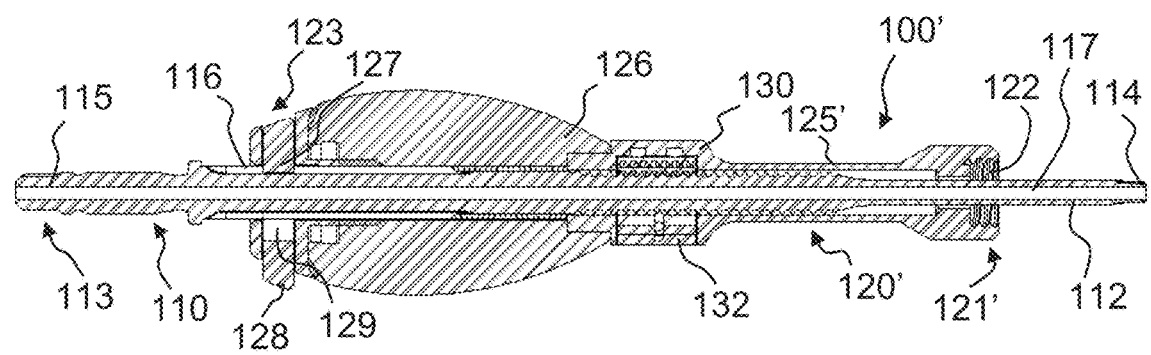
FIG. 12 is a cross-sectional view of the driver assembly of FIG. 11.
Figure 13:
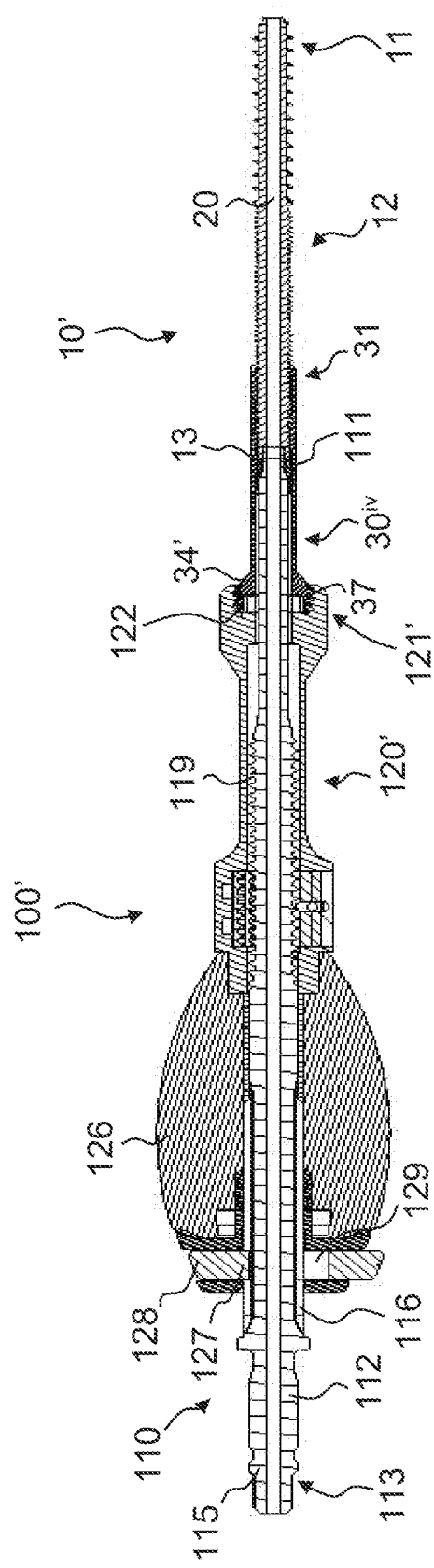
FIG. 13 is a cross-sectional view of the driver assembly of FIG. 11 engaged with the compression screw of FIG. 9.

Referring to FIGS. 11-13, a driver assembly 100' and method for inserting the compression screw 10' will be described. The driver assembly 100' is substantially the same as in the previous embodiment except for the distal end 121' of tubular body 125' of the compression sleeve driver 120'. Instead of a driver tip, the distal end 121' defines an internally threaded chamber 122 which threadably engages the threads 137 of the self-countersinking head 34'.

To insert the compression screw 10', the driver assembly 100' is positioned such that the driver tip 114 of the shaft 112 engages with the drive feature 22 of the bone screw 12 and the threads 137 of the self-countersinking head 34' are threadably received in the threaded chamber 122 of the compression sleeve driver 120', as shown in FIG. 13. During initial insertion, the connector switch 128 is moved to the engaged position such that the bone screw driver 110 and the compression sleeve driver 120' rotate together. The driver assembly 100' is rotated with both drivers 110, 120' rotating and thus the compression screw 10' is advanced as a single unit until the distal end 11 of the bone screw 12 is at a desired location. The thread engagement member 132 may be depressed during such rotation to ensure that the shaft 112 advances axially during the simultaneous rotation. If the distal end 31 of the compression sleeve 30$^{iv}$ contacts bone as the compression screw 10' is advanced, the cutting flutes 36 cut into the bone and the compression screw 10' is free to continue to advance as a single unit.

After the distal end 11 of the bone screw 12 has landed at the desired location, compression may be achieved by advancing the compression sleeve 30$^{iv}$ while the bone screw 12 remains stationary. The bone screw 12 remains stationary by holding the bone screw driver 110 stationary, for example, by attaching a locking device to the connection key 115, and by disengaging the connector switch 128. With the connector switch 128 moved to the disengaged position, the compression sleeve driver 120' rotates freely about the bone screw driver 110. Rotation of the compression sleeve driver 120' causes the compression sleeve 30$^{iv}$ to advance. Since the bone screw 12 is stationary as the compression sleeve driver 120' advances the compression sleeve 30$^{iv}$, the compression screw 10' shortens in length and the shoulder 35' and distal end 121' of the compression sleeve driver 120' thus apply compression. Again, the cutting flutes 36 on the compression sleeve distal end 31 allow the compression sleeve 30 to cut into and advance into the bone.

After the desired amount of compression has been reached, the head 34' may be countersunk. Countersinking is done by a third driver component (not shown) that mates with the compression sleeve driver feature 42. For example, the driver assembly 100 may be exchanged for the driver assembly 100' such that the driver tip 124 can be used to rotate the compression sleeve 30$^{iv}$ while the bone screw 12 is maintained stationary. As the compression sleeve 30$^{iv}$ advances over the bone screw 12, the threads 37 cut into the bone and advance the head 34' into a countersunk position within the bone.

Figure 14:
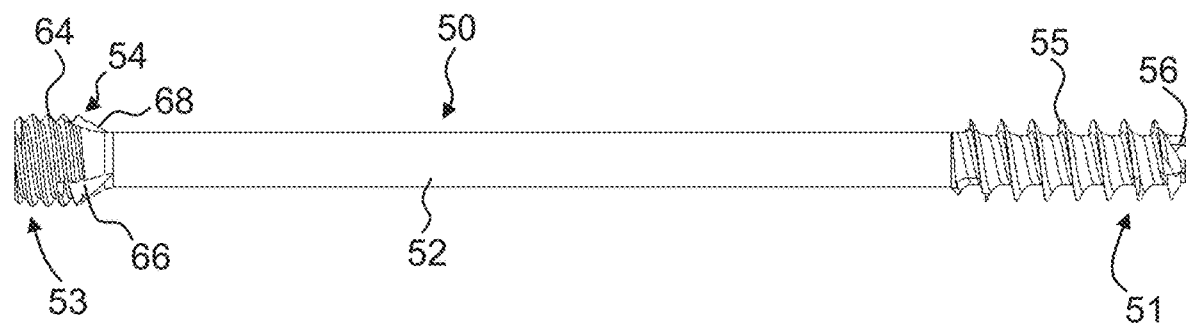
FIG. 14 is a plan view of a compression screw according to another embodiment of the invention.
Figures 15, 16:
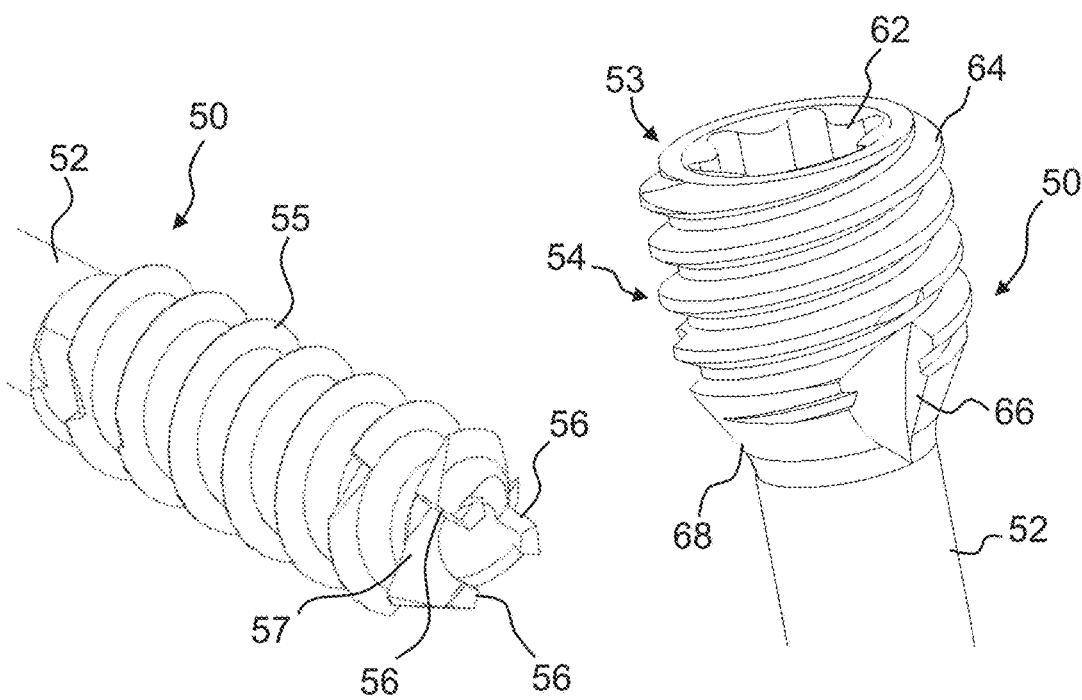
FIG. 15 is an expanded perspective view of the tip of the compression screw of FIG. 14.
FIG. 16 is an expanded perspective view of the head of the compression screw of FIG. 14.

Referring to FIGS. 14-16, a compression screw 50 in accordance with another embodiment will be described. The compression screw 50 includes a shaft 52 extending from a distal end 51 to a proximal end 53. A series of bone engaging threads 55 extend radially from the shaft 52 at the distal end 51. In the preferred embodiment, the bone engaging threads 55 are dual lead thread type, however, any type of thread may be used to facilitate the function of the compression screw 50. The distal end 51 preferably also includes at least one cutting flute 56 configured to cut into the bone as the compression screw 12 is rotated, defining a self-drilling and self-tapping tip. In a preferred embodiment, a slot 57 is associated with each cutting flute 56 to clear any chips, dust, or debris generated when the compression screw 50 is implanted into bone tissue.

The proximal end 53 of the shaft 52 includes a self-countersinking head 54. The self-countersinking head 54 has a tapered shoulder 68 and a series of external threads 64. The threads 64 may include one or more cutting flutes 66 such that the threads 64 are self-drilling and self-tapping. In the present embodiment, the threads 64 define a proximal rotary cutting structure. A drive feature 62 is defined in the proximal end 53 of the shaft 52 and is configured and dimensioned to be any shape that corresponds with the end of the driving instrument designed to engage the compression screw 50. As an example, in the illustrated embodiment, the drive feature 62 has a hexalobular configuration.

The shaft 52 between the bone engaging threads 55 and the head 54 is preferably free of threads. With this configuration, a difference in pitch between the bone engaging threads 55 and the threads 64 of the head 54 can provide additional compression control as the compression screw 50 is inserted. That is, if the pitch of the bone engaging threads 55 is larger than the pitch of the threads 64 of the head 54, and the fracture or joint line lies somewhere in the shaft 52 section of the screw 50, this configuration will provide compression between the two bones as the distal end 51 tries to advance faster than the head 54 of the screw 50.

Figure 17:
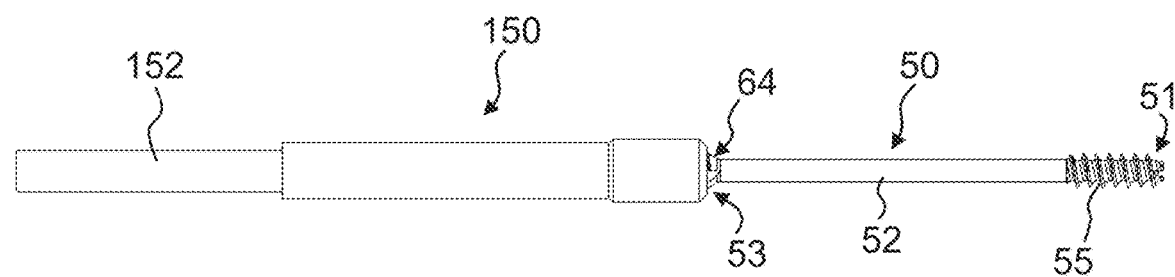
FIG. 17 is a plan view of an exemplary driver assembly engaging the compression screw of FIG. 14.
Figure 18:
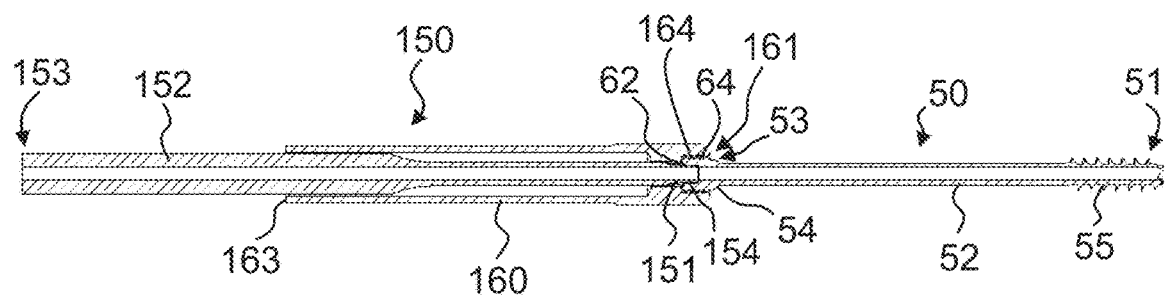
FIG. 18 is a cross-sectional view of the driver assembly of FIG. 17 engaged with the compression screw of FIG. 14.

Referring to FIGS. 17 and 18, a driver assembly 150 which allows the surgeon to further control how much compression is achieved will be described. The driver assembly 150 includes an inner driver member 152 and an outer driver member 160. The inner driver member 152 extends from a distal end 151 to a proximal end 153. A driver tip 154 is defined on the distal end 151 and is configured to engage the driver feature 62 of the compression screw 50.

The outer driver member 160 includes a tubular body extending from a distal end 161 to a proximal end 163. The distal end 161 defines a threaded chamber 164 configured to threadeably receive the threads 64 of the compression screw head 54.

To insert the compression screw 50, the driver assembly 150 is positioned with the driver tip 154 engaged with the driver feature 62 and the threads 64 of the head 54 threadably received in the threaded chamber 164. The inner and outer driver members 152, 160 are rotated such that the compression screw 50 is advanced. As the compression screw 50 advances, the distal end 161 of the outer driver member 160 will hit the near cortex and compress the fracture line as the screw 50 is continued to be inserted.

After the desired amount of compression has been reached, the inner driver member 152 is rotated, independent of the outer driver member 160, such that the compression screw 50 continues to advance with the outer driver member distal end 161 maintaining the compression. As the compression screw 50 advances, the threads 64 of the head 54 will enter the bone and begin to countersink the head 54. As the head 54 advances and countersinks, it simultaneously threads out of the threaded chamber 164. As explained before, the pitch of the bone engaging threads 55 and the threads 64 of the head 54 may be configured such that countersinking of the head 54 causes additional compression.

FIG. 19 is a cross-sectional view of a sleeve coupler attached to a compression screw and a ram driver according to another aspect of the present invention.

The VL (variable length) screw 10 of FIG. 19 is very similar to the VL screw 10 as shown in FIGS. 9-10 and similar elements will have the same reference numbers. The screw 10 allows for continuously controlled compression during and after screw placement as well as the ability to control the final length of the screw during implantation. Once the VL screw 10 is placed, continuous compression of the bone fragments is controlled by a surgeon using the compression sleeve 30 and/or a driver as will be explained below in more detail.

As shown in FIG. 19, the locking VL screw 10 functions by "locking" the bone screw 12 and compression sleeve 30 at a fixed length during insertion with a "ram" driver 190 that butts up against the back of the bone screw and prevents the rotation of the two screw components, thereby preventing translation of the bone screw into the compression sleeve. In other words, the ram driver 190 fixes the length or at least the minimum length of the compression screw 10.

Figure 21A:
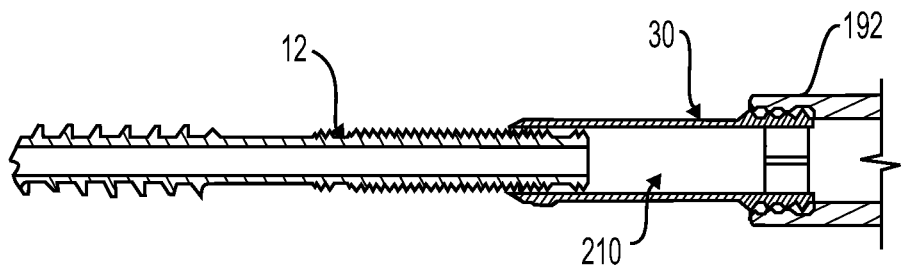
FIG. 21A is a cross-sectional view of a compression screw without the ram driver removed.
Figure 21B:
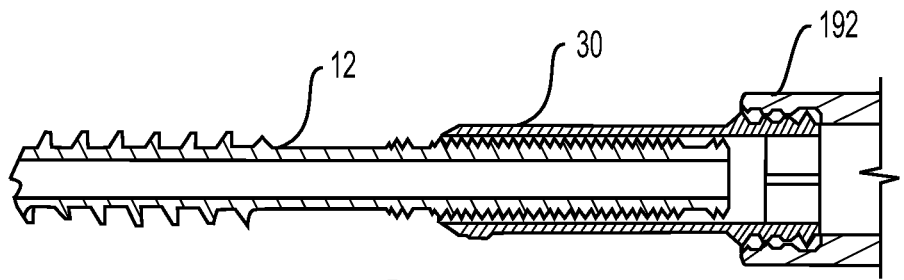
FIG. 21B is a cross-sectional view of a compression screw showing a shortened length.

After the locked compression screw 10 is inserted to the appropriate position in the bone, the screw is then "unlocked" by removing the ram driver 190. FIG. 21A shows the compression screw 10 in which the ram driver 190 has been removed to create the space 210 inside the compressions sleeve 30 and the compression sleeve can be advanced relative to the bone screw 12 to provide compression of the bone fragments. As the compression sleeve 30 is advanced, the proximal end 13 of the bone screw 12 translates proximally into the space 210 previously occupied by the ram driver 190 as shown in FIG. 21B. This solution reduces the overall size of the implant and simplifies the instrumentation used to insert the implant.

Also having external threads 37 on the compression sleeve 30 allows the compression sleeve to be buried below the surface of the bone to prevent irritation to the patient. The threads 37 gain purchase into the bone to prevent backout and maintain compression achieved by the screw 10. Instead of the compression sleeve 30 being a buttress, an instrument used to insert the screw 10 has a flat bottom which compresses the bone fragments together.

FIG. 20A is a perspective view of a compression screw and a fully assembled driver assembly comprising a sleeve coupler and a ram driver. FIG. 20B is a perspective view of a ram driver. FIG. 20C is a perspective view of a sleeve driver.

The sleeve coupler 192 is similar to the sleeve driver 120 as shown in FIGS. 11-12. As such, only the different components will be discussed herein. The sleeve coupler 192 threadably receives the external threading 18 of the compression sleeve 30. A button 194 is similar to the switch 128 of FIGS. 11-12. However, the button 194 is biased in a radial direction with a spring load. When the ram driver 190 is inserted into the sleeve coupler 192, a conically shaped annular rib/retaining feature 198 on its shaft 193 mates with the button 194 and is automatically locked. A handle 196 inserted into the connection key 115 provides leverage when turning the compression locked screw 10. Pushing of the button 194 disengages the lock and the ram driver 190 can then be removed from the sleeve coupler 192.

In the embodiment shown in FIGS. 20A-20C, a distal surface of the shaft 193 is flat/planar without any mating or drive feature such that it only butts up against the proximal end of the bone screw 12 without mating with the bone screw. In the embodiment shown, the flat surface is perpendicular to the longitudinal axis of the shaft 193.

Figure 22:
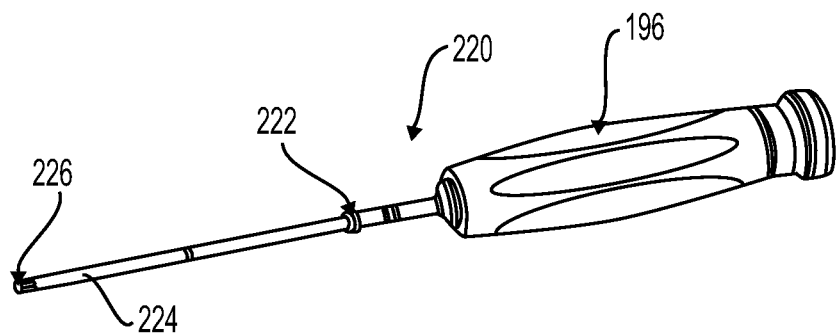
FIG. 22 is a perspective view of a countersink driver that can be coupled to the sleeve coupler of FIG. 23 illustrates cross-sectional front view of a side loading washer according to one aspect of the present invention.

FIG. 22 illustrates a countersink driver 220 that can be coupled to the sleeve coupler 192. The countersink driver 220 has the same retaining feature/conical annular rib 222 on its shaft 224 as that 198 of the ram driver. The distal end of the shaft 224 has a drive feature 226 such as a hexalobular configuration which is complementary to the drive feature 42 of the compression sleeve 30.

By relying on the ram driver 90 to lock the bone screw 12 and compression sleeve 30 together during insertion rather than a drive feature, the overall size and profile of the VL screw 10 can be significantly reduced to a desirable level. The present design also simplifies the instrumentation used to insert the implant.

A method of implanting a compression screw has three main steps: (1) insertion, (2) compression and (3) countersink. In the insertion step, the ram driver 190 is inserted into and is locked to the sleeve coupler 192. Then, the sleeve coupler 192 is threaded onto the compression sleeve 10 of the compression screw 10. The bone screw 12 is then rotated until the proximal end makes contact with the distal end of the ram driver shaft 193. The compression screw 10 is now ready for insertion into a bone. Clockwise turning of the handle 196 drives the locked compression screw 10 into the bone. When a desired depth has been reached, the insertion step is completed.

In the compression step, the compression sleeve 30 is translated relative to the bone screw 12 to shorten the overall length of the compression screw 10. In the embodiment shown, a ram lock 197 is unlocked by sliding such that the ram shaft 193 is free to translate. Continued turning of the handle in the same direction rotates the compression sleeve 30 relative to the bone screw 12 which compresses fragmented bones together. Once final compression is achieved, the ram driver 190 is removed from the sleeve coupler 192.

In an alternative compression method, the ram driver 190 may be removed and then the sleeve coupler 192 may be turned clockwise to rotate the compression sleeve 30 relative to the bone screw 12.

In the countersink step, after the final compression is achieved, the countersink driver 220 is inserted into the sleeve coupler until the retaining feature 222 travels past the lock 194. The shaft 224 is dimension such that when the countersink driver 220 is locked, the drive feature 226 is mated with the complementary drive feature 42 of the compression sleeve 30. Clockwise rotation of the handle 196 while holding the sleeve coupler 192 rotates and pushes the compression sleeve 30 into the bone. Once the distal end of the compression sleeve is at or below the bone surface, the sleeve coupler 192 and the locked countersink driver 220 are removed as a single unit.

Figure 23:
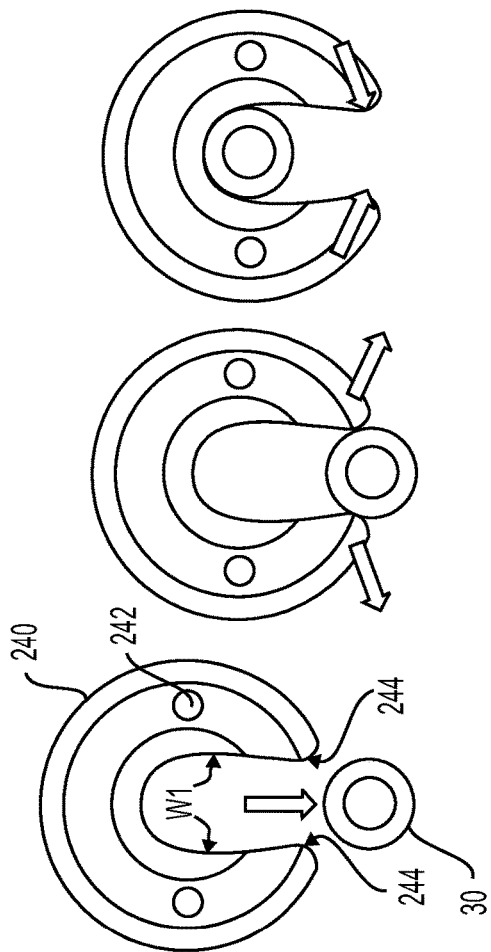

FIG. 23 illustrates cross-sectional front view of a side loading washer according to one aspect of the present invention.

Washers are often used with headed screws to provide a greater surface area for contact when compressing a fracture with the head of a screw. However, they can also be used for headless screws such as the compression screw 10. The larger surface spreads out the load over a greater surface area. A standard washer should be loaded onto the screw prior to insertion. If a washer is needed and was not assembled prior to insertion, the entire screw should be removed in order to assemble a washer onto the screw. This compromises the thread purchase and may result in the surgeon needing to move up to the next screw size to achieve fixation, adding operative time, frustration and ultimately, cost.

The side-loading retaining washer 240 can be assembled to the screw prior to or during insertion. The inner diameter W1 and slot of the washer is equal to or greater than the diameter of the mating screw shaft 30. There are two small retention bumps 244 near the end of the slot. The distance between these two retention bumps is smaller than the diameter of the screw shaft.

These retention bumps 244 splay open when pressed onto the screw shaft 30 and then collapse once the washer has been assembled. Once assembled to the screw 10, the washer 244 stays retained because the retention bumps 244 prevent disassembly as shown in FIG. 23.

Figure 24:
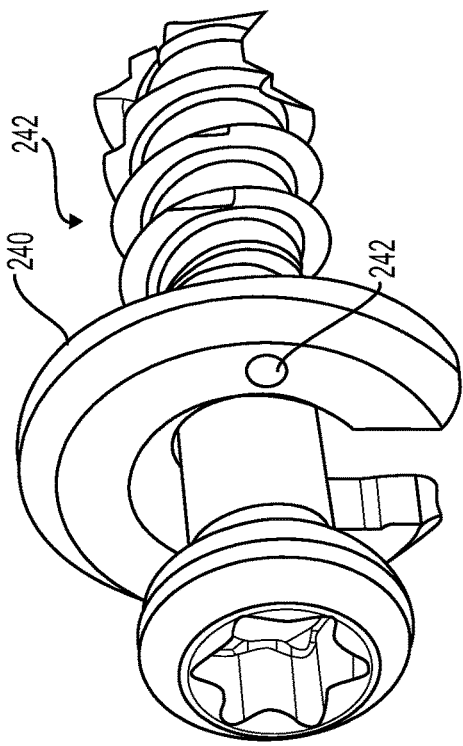
FIG. 24 is a perspective view of a side-loading retaining washer assembled onto a headed screw shaft according to another aspect of the present invention.

FIG. 24 is a perspective view of a headed screw 242 and the side-loading retaining washer 240 assembled on to the screw according to another aspect of the present invention.

Instead of a standard closed washer that should be assembled to the screw prior to insertion, the side-loading washer can be assembled to the headed screw at any time during insertion. This improves intra-operative versatility and reduces the risk of compromising thread purchase during the procedure.

Figure 25:
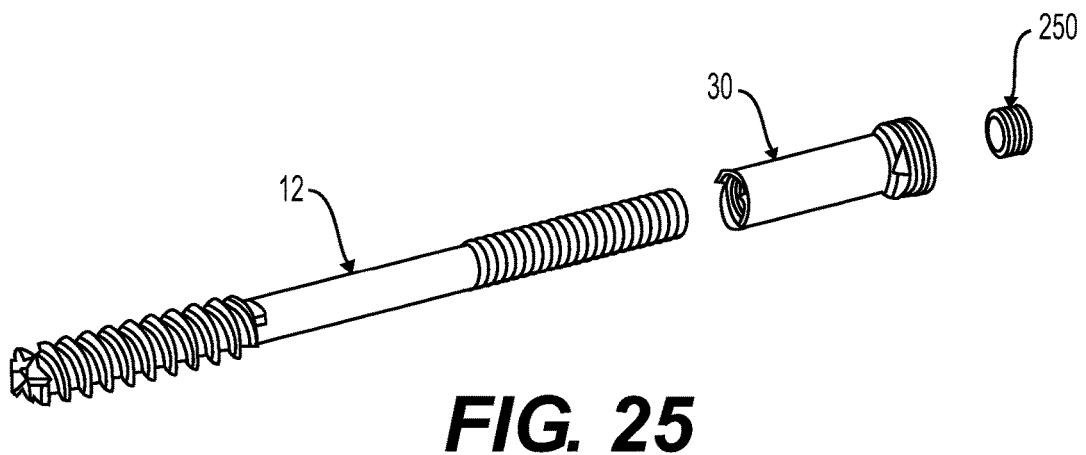
FIG. 25 is a perspective view of a jamming screw for locking the compression sleeve and bone screw according to another aspect of the present invention.

FIG. 25 is a perspective view of a jamming screw for locking the compression sleeve and bone screw according to another aspect of the present invention.

A jamming screw 250 is a small set screw that is inserted into the proximal end of the compression sleeve 30 and is bottomed out on the proximal end of the bone screw 12 post. This binds the two components of the compression screw 10 together to prevent disassembly. This jam screw 250 can have the same thread as the thread on the bone screw 12 post, a different pitch than the thread on the bone screw post, or a left-hand thread (vs. right-hand thread) to create this binding effect.

Adding a blind hole in the distal end of the compression sleeve 32 instead of a thru hole, paired with the jamming screw, limits the travel of the sleeve. The jamming screw 250 has a conventional drive feature and can be inserted and removed with a conventional screw driver having a complementary drive feature.

Figure 26:
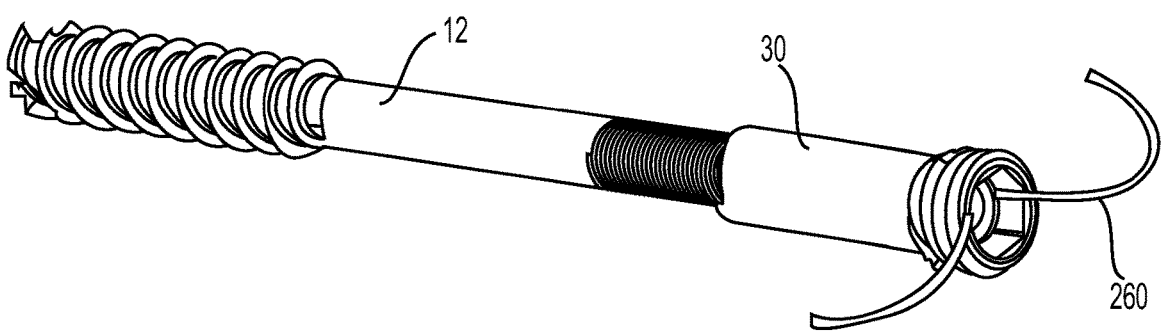
FIG. 26 is a perspective view of a jamming screw having a suture according to another aspect of the present invention.

FIG. 26 is a perspective view of a jamming screw having a suture 260 going through a through hole (not shown) and side grooves that interrupt the threading of the screw (see FIG. 28 for a similar feature). The suture 260 can be tied down to the surrounding anatomy. The suture 260 may be useful for fixing loose ligaments near the injury.

FIG. 27 is a perspective view of a breakaway jam screw 270. The breakaway jam screw 270 has a shaft 272, proximal end having a drive feature 274 and a jam screw 276. A breakaway region 278 is located just above the jam screw 276 and a distal end of the shaft 272, and has the smallest cross-sectional area for the entire screw 270.

By attaching the jam screw 276 to a larger protrusion, it will be easier to locate and use during surgery. There will be less concerns about losing the small jam screw 250 within the patient. The diameter of the breakaway region 278 is dimensioned in such a way that it always fails at a set torque value. This torque value is calculated using the polar moment of inertia. No undercut is necessary for the breakaway region because the jam screw is always contained within the sleeve once broken off. Having a breakaway region 278 allows the implant design to control the amount of torque applied to the jam screw 276 during final tightening of the implant. This will prevent overtightening or insufficient tightening of the implant components during locking.

Once the present compression screw 10 has been placed and it is time to lock the bone screw 12 post and compression sleeve 30 together, a driver is inserted into the drive feature 274 in the top of the breakaway screw 270. The screw is then inserted into the sleeve and tightened until a set torque is reached. Once the failure torque is reached, the breakaway section shears in torsion and leaves the jam screw within the sleeve, binding the post 12 to the sleeve 30.

FIG. 28 is a perspective view of a suture breakaway jam screw 280 having a shaft 282, jamming screw 286, and breakaway region 288. The suture jam screw 280 is the same as the breakaway jam screw 270, except that it has a distal side through-hole 280 and a pair of side grooves/channels 281 which interrupt the threading of the jamming screw 286. The through-hole 280 and side grooves 281 allow a suture to be attached to the jam screw 286 prior to insertion. After the jam screw 286 is broken off within the present compression screw 10, the suture 260 falls out the back of the compression sleeve 30 and can be tied down to the surrounding anatomy. This will allow the present compression screw 10 to be used as a type of suture button and will provide additional fixation to the screw head after placement.

FIGS. 29A and 29B are top view and perspective view of a bone screw, respectively, according to another aspect of the present invention. FIGS. 30A and 30B are top view and perspective view of a compression sleeve that mates with the bone screw of FIGS. 29A and 29B.

The compression screw 10 has a drive feature in both the proximal end of the bone screw 12 and compression sleeve 30. Both of these drive features needed to be engaged by a driver to insert the screw 10 in a locked state. Having a drive feature in the proximal end of the bone screw post required a larger outer diameter for the proximal end to account for the drive feature. This in turn led to a larger compression sleeve which mates to the bone screw post.

The two drive feature requirement made the screw size relatively large and needed to be decreased significantly. One aspect of the design as shown in FIGS. 29A and 29B is a novel method for insertion of a two-piece screw without the use of a traditional drive feature. This method relies on the interruption of the thread form between mating components to bind the screw at a fixed length for insertion.

To reduce the size of the compression sleeve 30, the drive feature in the bone screw 12 was replaced with three small cutouts 292 in the top of the bone screw threading 18. The cutouts 292 look like a cruciform drive, but with three cutouts instead of four.

The interruption of the threading 18 on the bone screw 290 can be seen in FIGS. 29A and 29B.

Three grooves 300 were then added to the distal end of the mating compression sleeve 302 which interrupt the internal threading of the compression sleeve. These grooves 300 are equivalent in size to the three cutouts 292 present on the bone screw 290 post. The depth of these grooves 300 is equivalent to the major diameter of the female thread present within the sleeve 30. These grooves 300 can be seen in FIGS. 30A and 30B.

As seen in FIG. 31, the compression screw 310 is then assembled such that the three cutouts 292 in the bone screw 290 post and the three grooves 300 in the compression sleeve 302 are circumferentially aligned with alignment markings 304. Prior to alignment, typically, the bone screw 290 would be rotated all the way. e.g., clockwise, until the screw bottoms out in the internal threading of the sleeve 302 such that the compressions screw 310 would be at its maximum length. Laser marking symbols 304 on either component can be used to aid alignment of the two components 302,290.

Although three cutouts 292 are shown, any number of cutouts could be used without departing from the spirit of the invention. For example, in one embodiment, the prongs 332 can be one to four in numbers, which means there will be corresponding number of cut outs to interrupt the threading.

Figure 33:
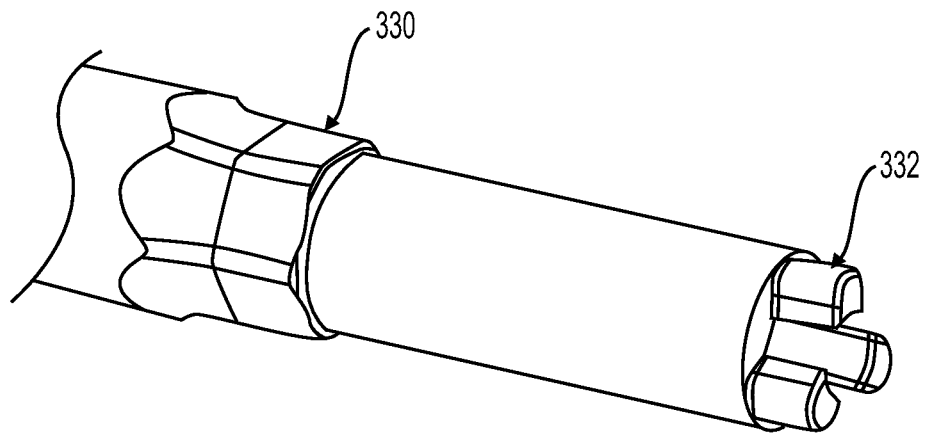
FIG. 33 is a perspective view of the driver having two spaced apart drive features according to another aspect of the present invention.
Figure 34:
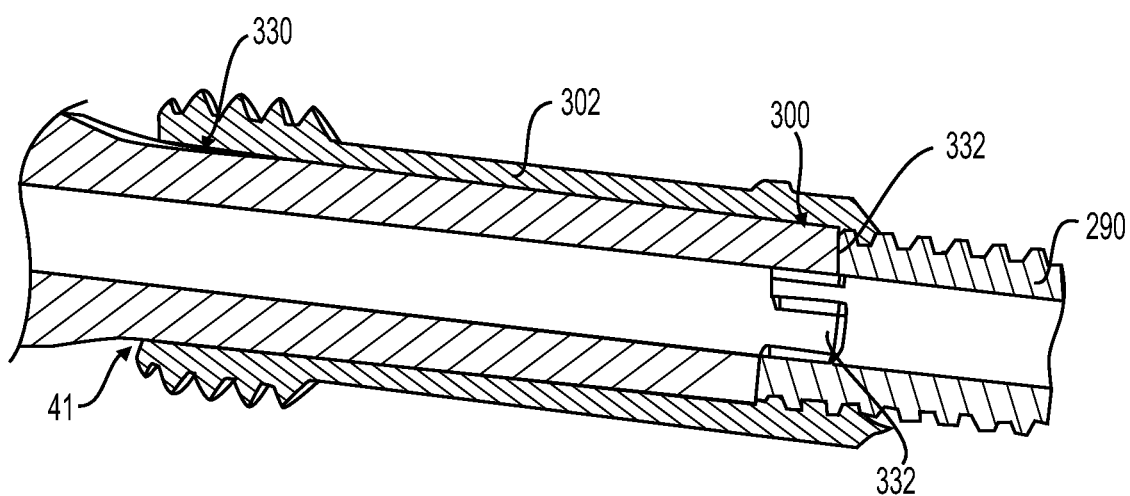
FIG. 34 is a cross-sectional view of the driver of FIG. 33 which has engaged the drive features of the compression sleeve and the bone screw according to another aspect of the present invention.

Once the three cutouts 292 and the three grooves 300 are circumferentially aligned, a single-piece driver 320 as shown in FIG. 32 is inserted into the screw 310. As shown in FIGS. 33 and 34, the driver 320 shaft has two separate drive features: a hex feature 330 which mates to the hex drive feature 42 in the head of the compression sleeve 310, and three prongs 332 which mate to the aligned features 300,292 between the bone screw 290 post and compression sleeve 302. The prongs 332 are positioned distally of the hex drive feature of 330 such that when the driver 320 is inserted into the compression screw 310, the two drive features mate with the respective drive features 41 and 292,300 to lock the compression sleeve 302 and bone screw 290 together.

Once the final position of the screw tip is achieved, a second driver such as the countersink driver 222 of FIG. 22 which only has the hex drive feature 226 that mates with the hex drive feature 41 of the compression sleeve 302, is used to countersink and compress the length of the screw 310.

By using the design that interrupts the thread form between the bone screw 290 post and compression sleeve 302, the relative size of the screw 310 was significantly reduced. This may improve surgical outcomes and use because the screw 310 could be used in more areas where a smaller size implant is very important. This method of insertion also simplifies the surgical procedure and instrumentation. The mating driver also does not use any complex mechanisms for insertion.

Although not shown in FIG. 32, the driver 320 may be used with the sleeve coupler 192 through its own retaining feature 198 that locks into the sleeve coupler lock 194 for locking the driver relative to the compression screw 10 to prevent the driver from inadvertently backing out of the screw.

Figure 35:
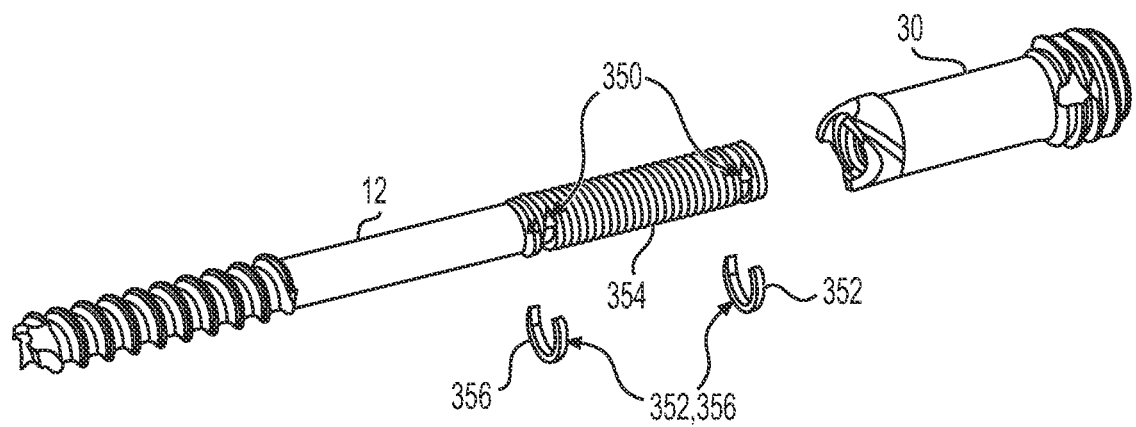
FIG. 35 is a perspective view of a compression screw having a pair of retaining clips according to another aspect of the present invention.
Figure 36:
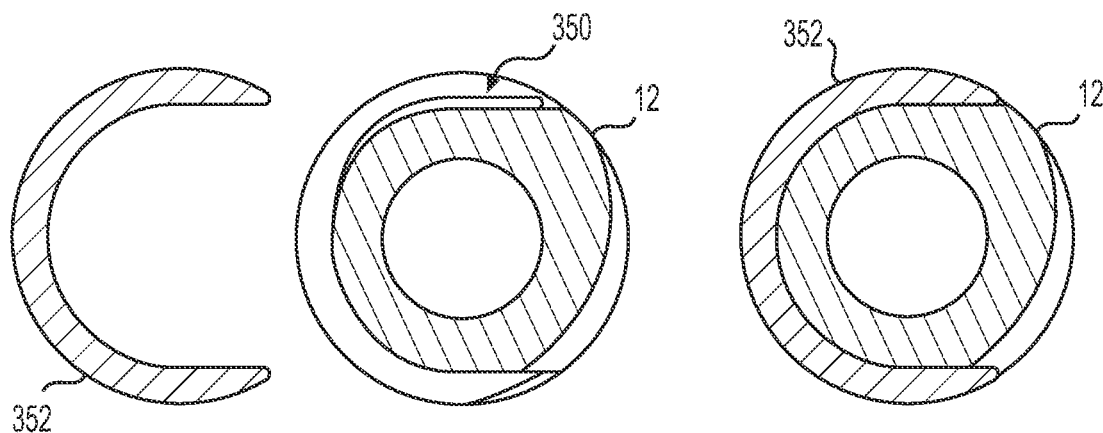
FIG. 36 shows cross-sectional views of the retaining c-clip and mating groove of the bone screw in a disassembled state and assembled state according to another aspect of the present invention.

FIG. 35 is a perspective view of a compression screw having a pair of retaining clips according to another aspect of the present invention. FIG. 36 shows cross-sectional views of the retaining c-clip 352 and mating groove of the bone screw in a disassembled state and assembled state.

The bone screw 12 has an external threading 354 which is threaded into an internal threading of the compression sleeve 30. The external threading 354 has a pair of mating grooves 350 that receive corresponding c-clips 352,356.

After threading the compression sleeve 30 onto the bone screw 12 post, the c-clip 352 is assembled into the groove 350 in the proximal end of the bone screw post. If the screw 10 is attempted to be disassembled, the c-clip 350 interrupts the thread form in the compression sleeve 30 and prevents the disassembly of the two components.

The outer diameter of each c-clip 352,356 is equal to or greater than the major diameter of the threads 354 on the proximal end of the bone screw 12 post and less than the minor diameter of the blind hole in the distal end of the compression sleeve 30.

A second c-clip 356 may be placed in a groove 350 further distal of the threaded shaft of the bone screw 12 post to limit the travel of the sleeve 30. The c-clips 352,356 are designed in such a way that they do not expand or collapse into the mating grooves 350.

The second c-clip 356 and even the first c-clip 352 may be laser welded to prevent disassembly. The c-clip is designed in such a way that it does not expand or collapse into the groove. The minor diameter of the c-clip is equivalent to or greater than the mating groove diameter.

The c-clips 352,356 advantageously prevent disassembly of the screw 30 prior to use, during use, or after implantation within the patient. There are numerous risks associated with utilizing a device that has the potential to disassemble during a surgical procedure. Addressing these risks will reduce the risk to an acceptable level.

Limiting the travel of the sleeve 30 along the length of the bone screw 12 post (reducing the overall length of the screw 10) also improves the ability of the implant to consistently countersink below the surface of the bone and achieve its final targeted length. If no method was applied to limit the amount of travel, the proximal end of the sleeve 30 could fall below the proximal end of the bone screw 12 post, which could potentially force the driver off of the screw preventing further countersinking or removal due to lack of a drive feature.

Figure 37:
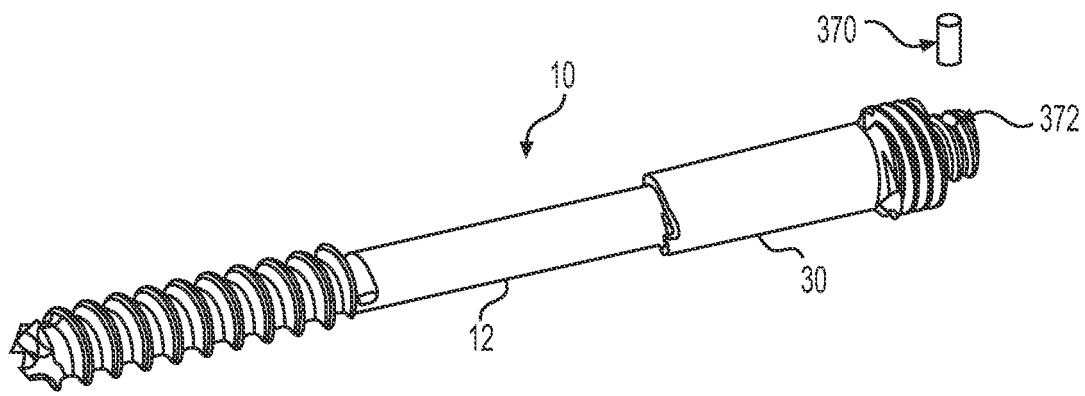
FIG. 37 is a perspective view of a compression screw with a pin for limiting travel according to another aspect of the present invention.
Figure 38:
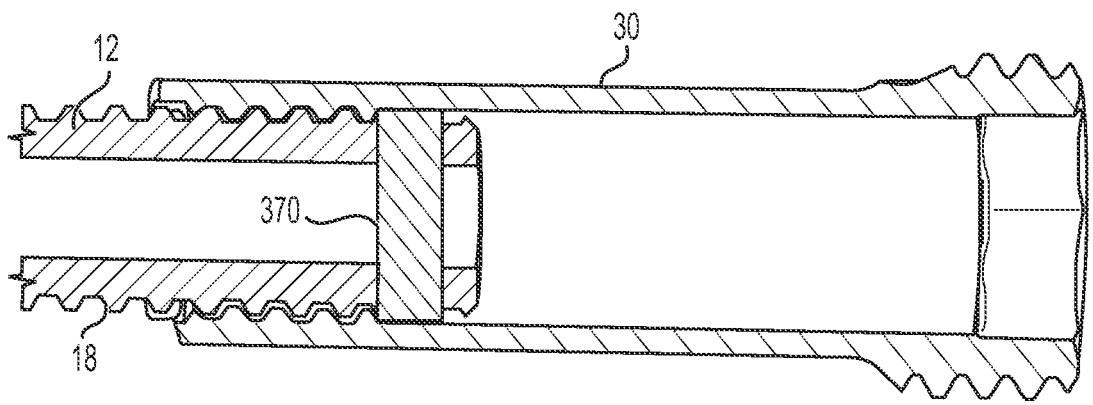
FIG. 38 is a cross-sectional view of the compression screw 10 and the pin of FIG. 37.

FIG. 37 is a perspective view of a compression screw with a pin for limiting travel according to another aspect of the present invention. FIG. 38 is a cross-sectional view of the compression screw 10 and the pin of FIG. 37.

After threading the compression sleeve 30 onto the bone screw 12 post, a pin 370 is pressed through a thru hole 372 (normal to the axis of the screw) in the proximal end of the bone screw post. The length of the pin is equal to the major diameter of the threads on the proximal end of the bone screw post and less than the minor diameter of the blind hole in the distal end of the compression sleeve. The pin 370 interrupts the thread form and prevents disassembly of the two components. Although not shown, a second pin 370 can also be placed in a second thru hole down the threaded shaft of the bone screw 12 post to limit the travel of the sleeve 30. Thus, instead of the mating grooves 350 as shown in FIG. 35, there would be two through holes and instead of the c-clips 352,356, there would be two pins 370.

Figure 39:
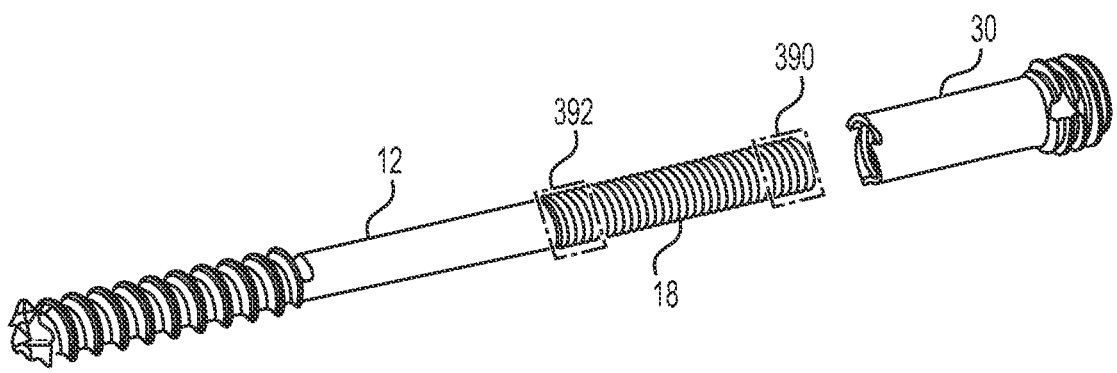
FIG. 39 shows a perspective view of a compression screw with deformed threading according to another aspect of the present invention.

FIG. 39 shows a perspective view of a compression screw with deformed threading according to another aspect of the present invention.

After threading the compression sleeve 30 onto the bone screw 12 post, a proximal portion 390 of the threads 18 is deformed utilizing a variety of methods (swaging, end-forming, knurling, and the like). The deformation of the threads prevents the disassembly of the components 12,30. An additional deformed portion 392 distal of the proximal portion 390 may be formed on the threading 18 of the bone screw 12 post to limit the travel of the sleeve 30.

Figure 40:
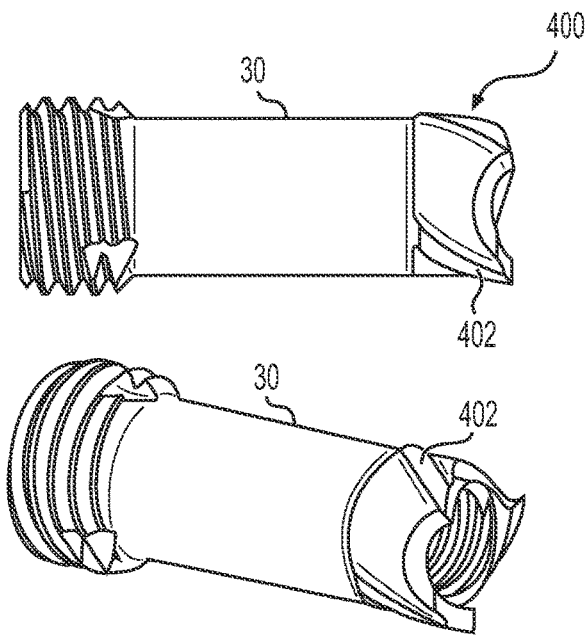
FIG. 40 show a side view and perspective view of a compression sleeve having a distal drill tip according to yet another aspect of the present invention.
Figure 41:
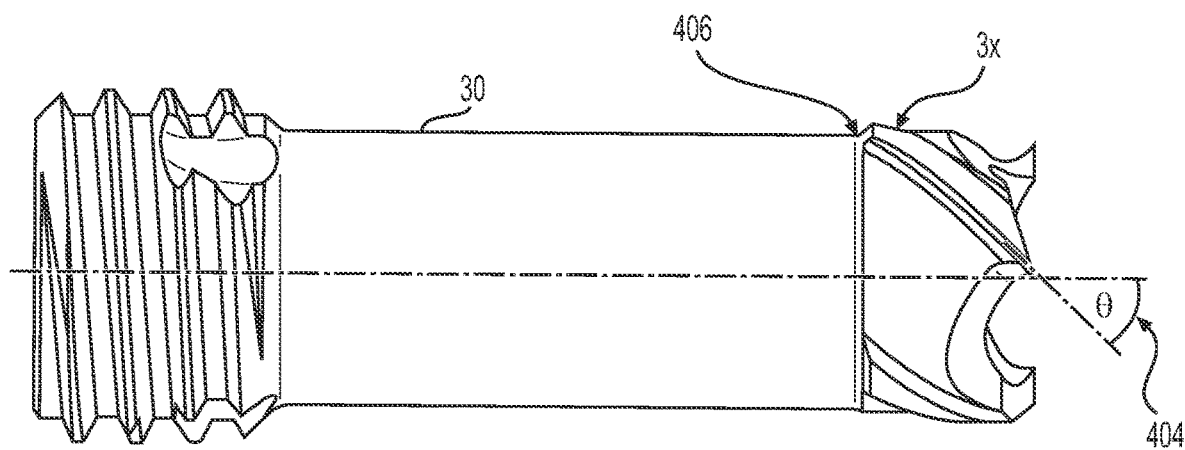
FIG. 41 is a side view of the compression sleeve of FIG. 39.

FIG. 40 show a side view and perspective view of a compression sleeve having a distal drill tip according to yet another aspect of the present invention. FIG. 41 is a side view of the compression sleeve of FIG. 39.

A drill tip 400 geometry of the sleeve 30 optimizes the cutting ability of the sleeve and improve insertion of the screw 10. By optimizing the cutting ability, the screw 10 gains better purchase and achieve greater compression.

The drill tip 400 geometry includes a drill margin (e.g., 3× margin), cutting flutes 402 which define slots through which cut bone is evacuated proximally, and lip relief (e.g., 5-25 degrees) 406 located on the tip of the compression sleeve 30 which mates to the bone screw 12 post.

This drill tip geometry improves the cutting ability of the compression sleeve 30 and evacuates the bone centrifugal to the sleeve (like a drill) instead of pushing it forward. The bone fills in the space behind the drill tip 400 to provide better thread purchase for the threads on the compression sleeve 30.

The outer diameter of the drill tip is equal to or less than the minor diameter of the threads on the compression sleeve. The rake angle is the angle between the flute 402 and longitudinal axis of the sleeve 30. The rake angle on the drill point sleeve can be between 0° (parallel) and 45° (positive), but more particularly 5-25 degrees. The margin is the trailing edge of the cutting surface. The drill tip 400 has three margins to allow for better self-centering of the compression sleeve 30 during insertion than a single or double margin drill geometry. The compression sleeve 30 tapers to a smaller diameter behind the drill tip geometry (see taper portion 406 in FIG. 406) to provide clearance and reduce friction. Thus, the diameter of the drill tip 400 is large than that of the shaft of the compression sleeve 30.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as defined in the claims.

What is claimed is:

1. A variable length headless compression screw insertion system comprising:
   a compression screw having a bone screw and a compression sleeve coupled to the bone screw, wherein:
      the bone screw including a proximal end having an external threading threadably received in the compression sleeve, and
      the compression sleeve includes a proximal end having a predefined drive feature and an external threading;
   a driver assembly for driving the compression screw into a bone and including:
      a sleeve coupler adapted to threadably receive the external threading of the compression sleeve;
      a ram driver adapted to be coupled to the sleeve coupler and having a predetermined length such that its distal end is shaped to contact the proximal end of the bone screw to prevent translation of the bone screw relative to the compression sleeve
      wherein the proximal end of the bone screw lacks a drive feature and the distal end of the ram driver has a flat surface to contact the proximal end of the bone screw to prevent translation of the bone screw, but allow rotation of the bone screw relative to the compression sleeve.

2. The system of claim 1, wherein the distal end of the ram driver has a flat surface to contact the proximal end of the bone screw to lock the bone screw to the compression sleeve without mating with the bone screw.

3. The system of claim 1, wherein the driver assembly further comprises a sleeve driver adapted to be coupled to the sleeve coupler and having a predetermined length such that its distal end has a complementary drive feature that mates with the predefined drive feature of the compression sleeve, the sleeve driver adapted to rotate the compression sleeve relative to the sleeve coupler.

4. The system of claim 1, wherein:
   the sleeve coupler includes a housing having a lock; and
   the ram driver includes an annular rib adapted to lock to the sleeve coupler lock such that the distal end of the ram driver is translationally fixed relative to the compression sleeve.

5. A variable length headless compression screw insertion system comprising:
   a compression screw having a bone screw and a compression sleeve coupled to the bone screw, wherein:
      the bone screw includes a distal end having a series of bone engaging threads and shaped to be self-drilling and self-tapping, and a proximal end having an external threading threadably received in the compression sleeve, and
      the compression sleeve includes a distal end threadably receiving the bone screw and a proximal end having a predefined drive feature and an external threading;
   a driver assembly for driving the compression screw into a bone and including:
      a sleeve coupler adapted to threadably receive the external threading of the compression sleeve;
      a ram driver adapted to be coupled to the sleeve coupler and having a predetermined length such that its distal end is shaped to contact the proximal end of the bone screw to prevent translation of the bone screw relative to the compression sleeve; and
      a sleeve driver adapted to be coupled to the sleeve coupler and having a predetermined length such that its distal end has a complementary drive feature that mates with the predefined drive feature of the compression sleeve, the sleeve driver adapted to rotate the compression sleeve relative to the sleeve coupler.

6. The system of claim 5, wherein the distal end of the ram driver has a flat surface to contact the proximal end of the bone screw to lock the bone screw to the compression sleeve to prevent translation of the bone screw, but allow rotation of the bone screw relative to the compression sleeve.

7. The system of claim 5, wherein the proximal end of the bone screw lacks a drive feature and the distal end of the ram driver has a flat surface to contact the proximal end of the bone screw to prevent translation of the bone screw, but allow rotation of the bone screw relative to the compression sleeve.

8. The system of claim 5, wherein:
   the sleeve coupler includes a housing having a lock; and
   the ram driver includes an annular rib adapted to lock to the sleeve coupler lock such that the distal end of the ram driver is translationally fixed relative to the compression sleeve.

* * * * *